United States Patent [19]
Hinnenkamp et al.

[11] Patent Number: 5,814,098
[45] Date of Patent: Sep. 29, 1998

[54] ADJUSTABLE SIZING APPARATUS

[75] Inventors: Thomas F. Hinnenkamp, White Bear Lake; Mark A. Blazei, Coon Rapids; Jonathan Kagan, Minneapolis; Brian M. Packard, Monticello; Ricci D. Smelser, Maple Lake; David M. Costello, Waconia; Angela L. Hillyard, Crystal; Tim T. Hidani, Plymouth, all of Minn.

[73] Assignee: St. Jude Medical, Inc., St. Paul, Minn.

[21] Appl. No.: 656,895

[22] Filed: Jun. 3, 1996

Related U.S. Application Data

[63] Continuation-in-part of Ser. No. 477,136, Jun. 7, 1995, abandoned.

[51] Int. Cl.$^6$ ............................... A61F 2/24; A61F 2/76
[52] U.S. Cl. ................................ 623/2; 128/774; 33/512; 33/555.2
[58] Field of Search ............... 623/2, 900; 128/774, 128/778, 780; 33/511, 512, 514.2, 501.45, 555.2

[56] References Cited

U.S. PATENT DOCUMENTS

| | | | |
|---|---|---|---|
| 740,943 | 10/1903 | Summersby | 33/514.2 |
| 1,339,896 | 5/1920 | Kemper . | |
| 3,661,148 | 5/1972 | Kolin | 128/2.05 P |
| 3,707,146 | 12/1972 | Cook et al. | 128/780 |
| 3,738,355 | 6/1973 | Salvatore | 128/2 S |
| 4,211,241 | 7/1980 | Kaster et al. | 128/774 |
| 4,328,811 | 5/1982 | Fogarty | 128/774 |
| 4,453,434 | 6/1984 | Lissy | 81/57.29 |
| 4,566,466 | 1/1986 | Ripple et al. | 128/781 |
| 4,602,911 | 7/1986 | Ahmadi et al. | 623/2 |
| 4,643,194 | 2/1987 | Fogarty | 128/668 |
| 4,685,474 | 8/1987 | Kurz et al. | 128/778 |
| 4,721,507 | 1/1988 | Chin | 128/774 |
| 4,972,845 | 11/1990 | Iversen et al. | 128/774 |
| 5,010,892 | 4/1991 | Colvin et al. | 128/774 |
| 5,042,161 | 8/1991 | Hodge | 33/501.45 |
| 5,327,908 | 7/1994 | Gerry | 128/774 |
| 5,353,513 | 10/1994 | Round | 73/555.2 |
| 5,360,014 | 11/1994 | Sauter et al. | 128/774 |
| 5,489,296 | 2/1996 | Love et al. | 623/2 |
| 5,607,446 | 3/1997 | Beechler et al. | 606/198 |

OTHER PUBLICATIONS

Brochure: "Flexibility for Inflexible Chests: Bendable Sizer Set Model 903", St. Jude Medical, St. Paul, Minnesota, Feb. 1990.

Primary Examiner—John G. Weiss
Assistant Examiner—Bruce E. Snow
Attorney, Agent, or Firm—Westman, Champlin & Kelly, P.A.

[57] ABSTRACT

The present invention is a single apparatus that can be adjusted through a range of diameters to measure an anatomical tissue annulus. The apparatus includes an elongated support member having a proximal end and a distal end. An operator actuated movable member is joined to the proximal end of the elongated support member while an adjustable member is joined to the distal end of the elongated support member. The adjustable member has a reference axis and an outer curved surface selectively positionable in response to the operator actuated member. In particular, the outer curved surface can be selectively positioned between an inner position proximate the reference axis and an outer position spaced apart from the reference axis.

12 Claims, 27 Drawing Sheets

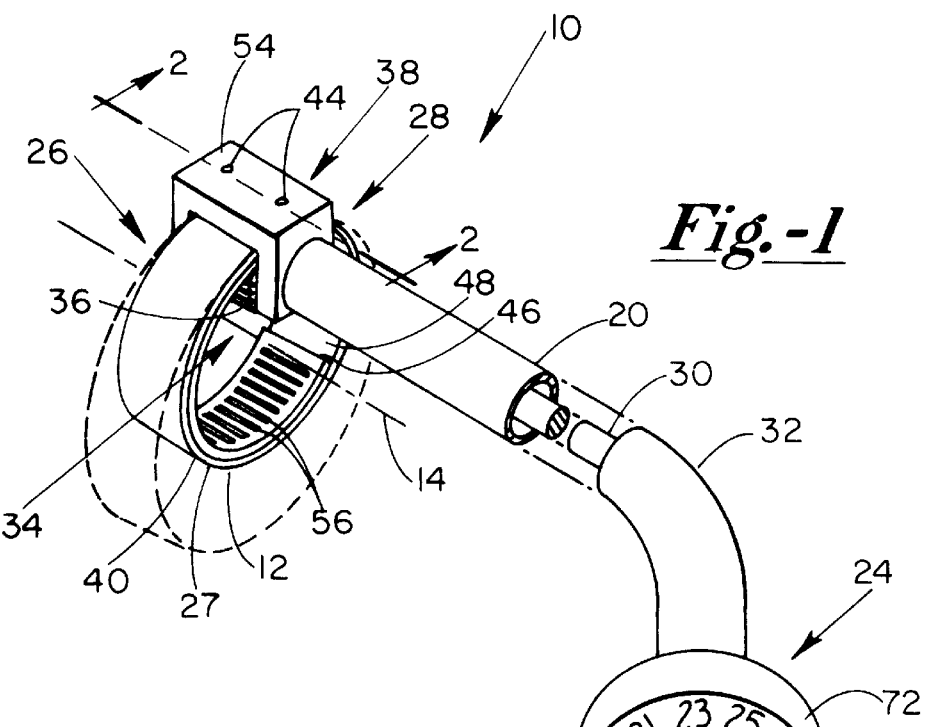
_Fig.-1_
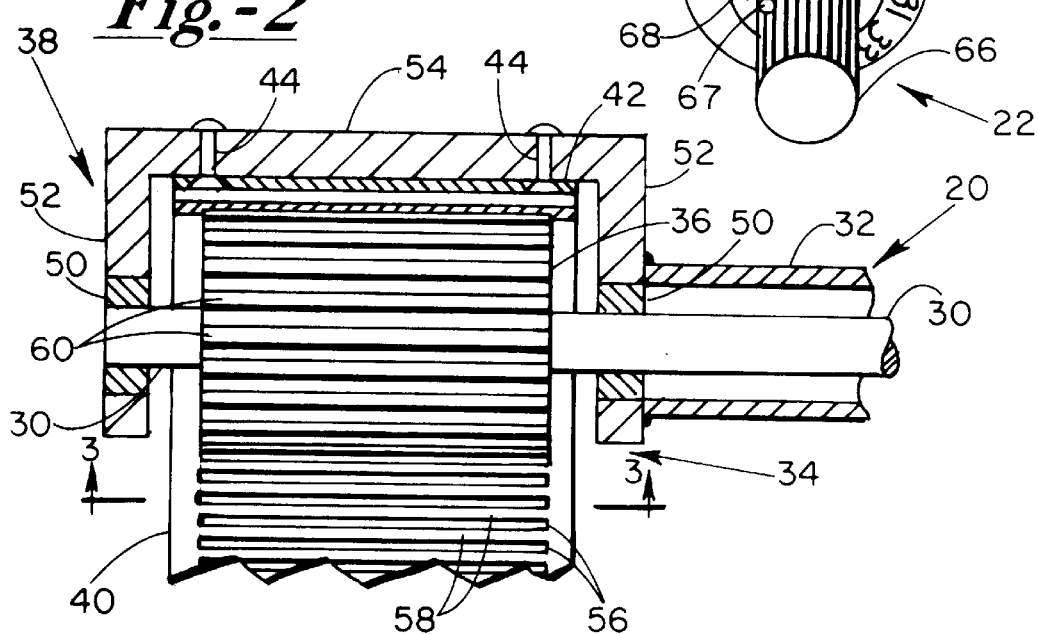
_Fig.-2_
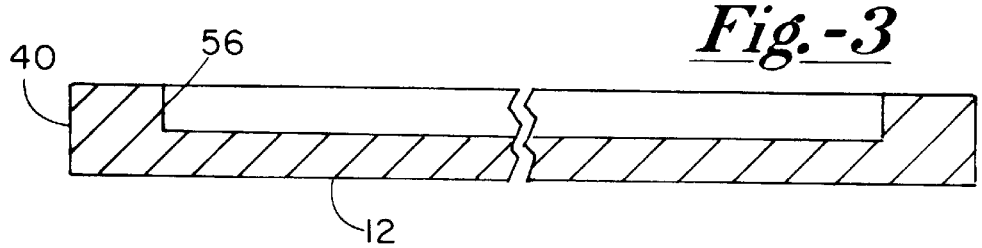
_Fig.-3_

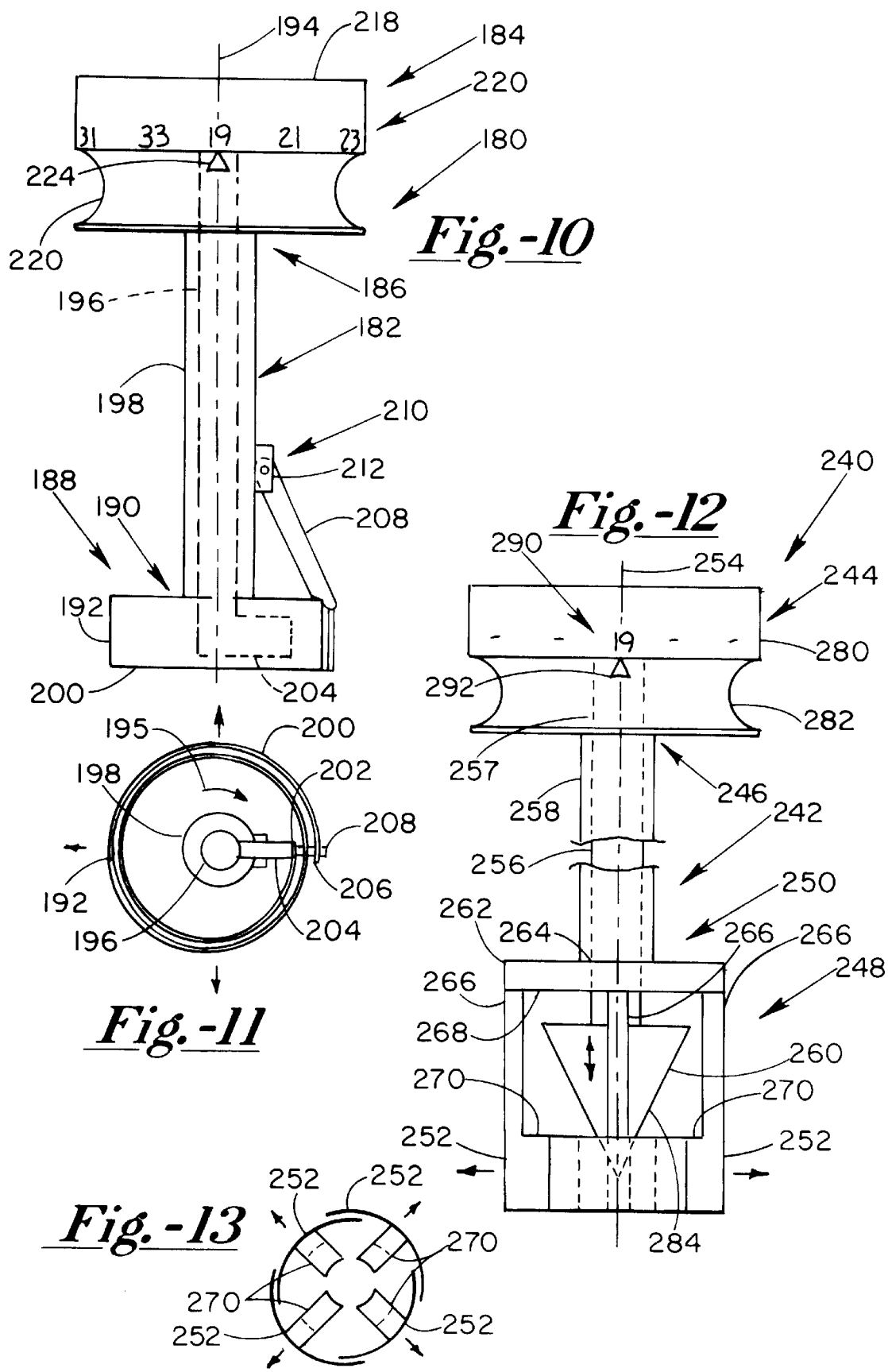

ADJUSTABLE SIZING APPARATUS

CROSS REFERENCE TO RELATED APPLICATION

This application is a continuation-in-part of application Ser. No. 08/477,136, filed Jun. 7, 1995 now abandoned.

FIELD OF THE INVENTION

The present invention relates to an apparatus for measuring an inner diameter of an anatomical tissue annulus. More particularly, the invention relates to an apparatus used to measure a site where a prosthetic heart valve will be implanted.

BACKGROUND OF THE INVENTION

An implantable prosthetic heart valve is used as a replacement for a native heart valve of a patient. A typical prosthetic heart valve includes an annular valve orifice or body to provide a passageway for blood. At least one and usually two leaflets are mounted to an inner surface of the annular valve body and open or close with the flow of blood through the passageway.

A suture ring or sewing cuff is used to sew the heart valve to the patient's heart tissue. The sewing cuff is secured about the heart valve body in a circumferential groove and generally includes a biocompatible fabric suitable for allowing a needle and suture to pass therethrough. The sewing cuff is placed proximate the tissue annulus at the site of the excised native heart valve. Sutures are passed through the tissue annulus and the sewing cuff and tied snugly, thereby securing the valve to the heart.

Prosthetic heart valves are implanted wholly or partially within the tissue annulus of the excised native valve. To assure proper fit of the valve to the patient, the patient's tissue annulus must be "sized" to indicate the size of the valve to be implanted. In particular, proper fit of the annular valve body within the tissue annulus of the excised native valve is required. Commonly, a set of sizers is supplied by the prosthetic heart valve manufacturer corresponding to the different sizes of available prosthetic heart valves. After excision of the native valve, an attending physician uses the sizers to determine which corresponding prosthetic heart valve will be implanted. In order to assure that the proper prosthetic heart valve will be used, the attending physician usually must attempt to size the annulus several times with one or more sizers of different diameters until the best fit is recognized. The sizing procedure consumes valuable time during the operation.

Although described above with respect to a tissue annulus formed by excising a native heart valve, measurement of other anatomical tissue annuli such as arteries, veins and an esophagus, is desirable.

SUMMARY OF THE INVENTION

The present invention is a single apparatus that can be adjusted through a range of diameters to measure an anatomical tissue annulus. The apparatus includes an elongated support member having a proximal end and a distal end. An operator actuated movable member is joined to the proximal end of the elongated support member while an adjustable member is joined to the distal end of the elongated support member. The adjustable member has a reference axis and an outer curved surface selectively positionable in response to the operator actuated member. In particular, the outer curved surface can be selectively positioned between an inner position proximate the reference axis and an outer position spaced apart from the reference axis.

In an embodiment, the elongated support member includes a bore extending from the proximal end to the distal end. A rotatable shaft is positioned within the bore and extends therein connecting the operator actuated movable member to the adjustable member. Rotation of the operator actuated movable member allows the outer curved surface of the adjustable member to be selectively displaced as discussed above.

Preferably, an indicator is mounted to the elongated support member. The indicator includes indicia representative of selected radial distances of the outer curved surface from the reference axis. A detent mechanism rotates with the shaft and selectively engages releasable stop surfaces on the indicator. The stop surfaces correspond to the various indicia on the indicator. The stop surfaces hold the shaft in each of the selected angular positions, which in turn, maintains the outer curved surface at each selected radial distance from the reference axis.

Another embodiment of the present invention relates to an apparatus for sizing a tissue annulus. The apparatus comprises a pair of elongated support members that are pivotally joined together, and an adjustable member that is supported on a distal end of each elongated support member. The adjustable member has a reference axis and an outer curved surface selectively positionable in response to the pivotal displacement of the elongated support members between an inner position proximate the reference axis and an outer position spaced apart from the reference axis.

Another aspect of the present invention relates to a method for sizing a tissue annulus. The method comprises the steps of placing a balloon proximate the tissue annulus and filling the balloon with a fluid to expand the balloon and engage an outer surface of the balloon with the tissue of the excised heart.

BRIEF DESCRIPTION OF THE DRAWINGS

FIG. 1 is a perspective view of a first embodiment of the present invention with a portion broken away;

FIG. 2 is a sectional view of the first embodiment taken along lines 2—2 of FIG. 1;

FIG. 3 is an enlarged sectional view of a flexible band;

FIG. 10 is a side elevational view of a fourth embodiment of the present invention;

FIG. 11 is a bottom plan view of the fourth embodiment;

FIG. 12 is a side elevational view of a fifth embodiment of the present invention with a portion broken away;

FIG. 13 is a diagrammatic view of movable elements of the fifth embodiment;

DETAILED DESCRIPTION OF THE PREFERRED EMBODIMENTS

The following description of embodiments of the present invention will be described with particular reference to sizing a tissue annulus of an excised native heart valve. It should be understood that the embodiments of the present invention can also be used to measure other tissue annuli such as an artery, a vein, and an esophagus.

Figure 8A:
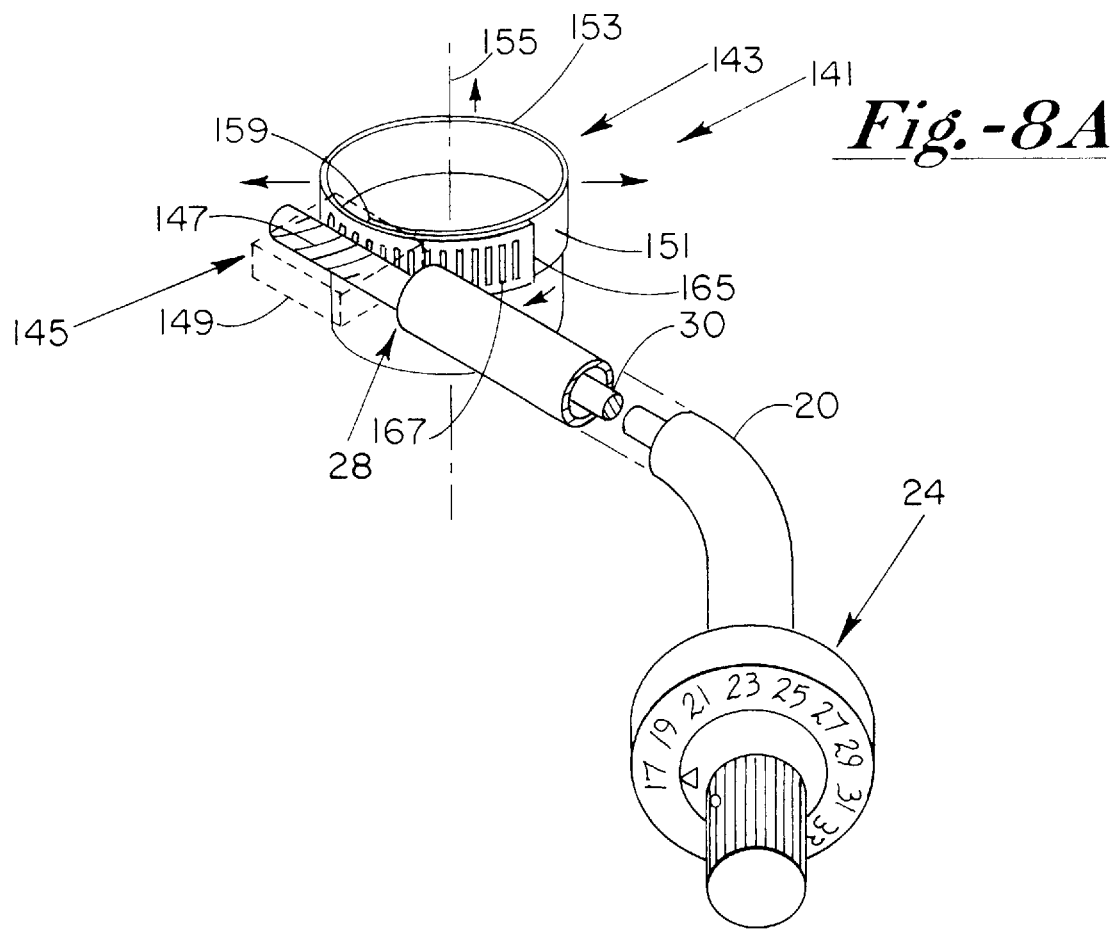
FIG. 8A is a perspective view of a second embodiment of the present invention with portions broken away.
Figure 8:
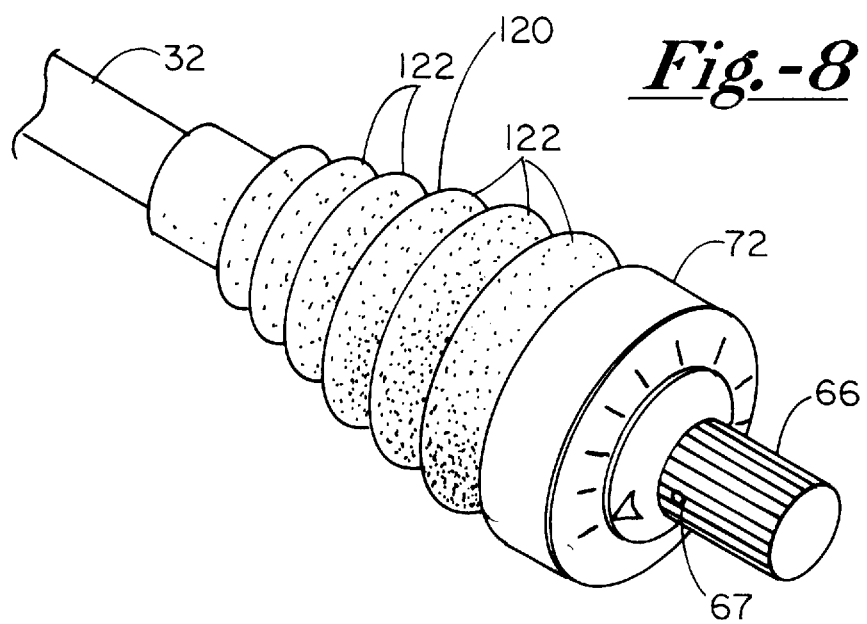
FIG. 8 is a perspective view of a handle for the first embodiment of the present invention.

FIGS. 1 and 8 illustrate a first embodiment of a sizing apparatus 10 of the present invention suitable for sizing a tissue annulus of a heart 18 to correlate with the size of a prosthetic heart valve (not shown). As will be described below regarding this embodiment and all embodiments to follow, the sizing apparatus includes an outer surface, preferably curved, that expands and contracts radially from a reference axis to measure a tissue annulus 16 of the heart 18 where the prosthetic heart valve will be positioned so that the surgeon or other medical personnel know the correct size of the prosthetic heart valve to implant.

Preferably, the outer surface 12 contacts the tissue annulus 16 at multiple points, preferably greater than two points or positions. In this manner, distortion of the tissue annulus 16 is minimized and the tissue annulus 16 remains substantially circular. Distortion of the tissue annulus 16 from its substantially circular shape may give misleading measurements. By using cylindrical bands or an expandable member described below, contact is made substantially about the complete inner surface of the tissue annulus 16 to minimize distortion. However, heart tissue is flexible and will retain its shape after distortion. Currently, prosthetic heart valves have an outside diameter ranging from 17 mm to 33 mm, although smaller and larger heart valves are also available. Indica on the sizing apparatus or a plate with apertures is preferably provided in all of these embodiments to correlate to the sizes of available prosthetic heart valves.

Generally, the sizing apparatus 10 includes an elongated support member 20 that couples an operator actuated movable member 22 to an adjustable member 26. The operator actuated movable member 22 is mounted to a proximal end 24 of the elongated support member 20, while the adjustable member 26 is mounted at a distal end 28 of the elongated support member 20. In particular, the adjustable member 26 responds to movements of the operator actuated movable member 22 so as to selectively displace the outer surface 12 toward or away from the reference axis 14.

Referring to FIGS. 1 and 2, the elongated support member 20 includes a shaft 30 that is rotatable within an outer support casing 32. The adjustable member 26 includes a drive assembly 34 having a rotatable drive element, preferably, a gear 36, mounted to the shaft 30 for rotation therewith and a housing 38 for supporting the gear 36. The gear housing 38 is secured to the outer support casing 32. The shaft 30 is rotatably mounted to the housing 38 with suitable bearing assemblies So provided in extending support plates 52 of the gear housing 38. The support plates 52 are joined together by a plate portion 54 upon which the first end 42 of the flexible band 40 is attached.

Figure 7:
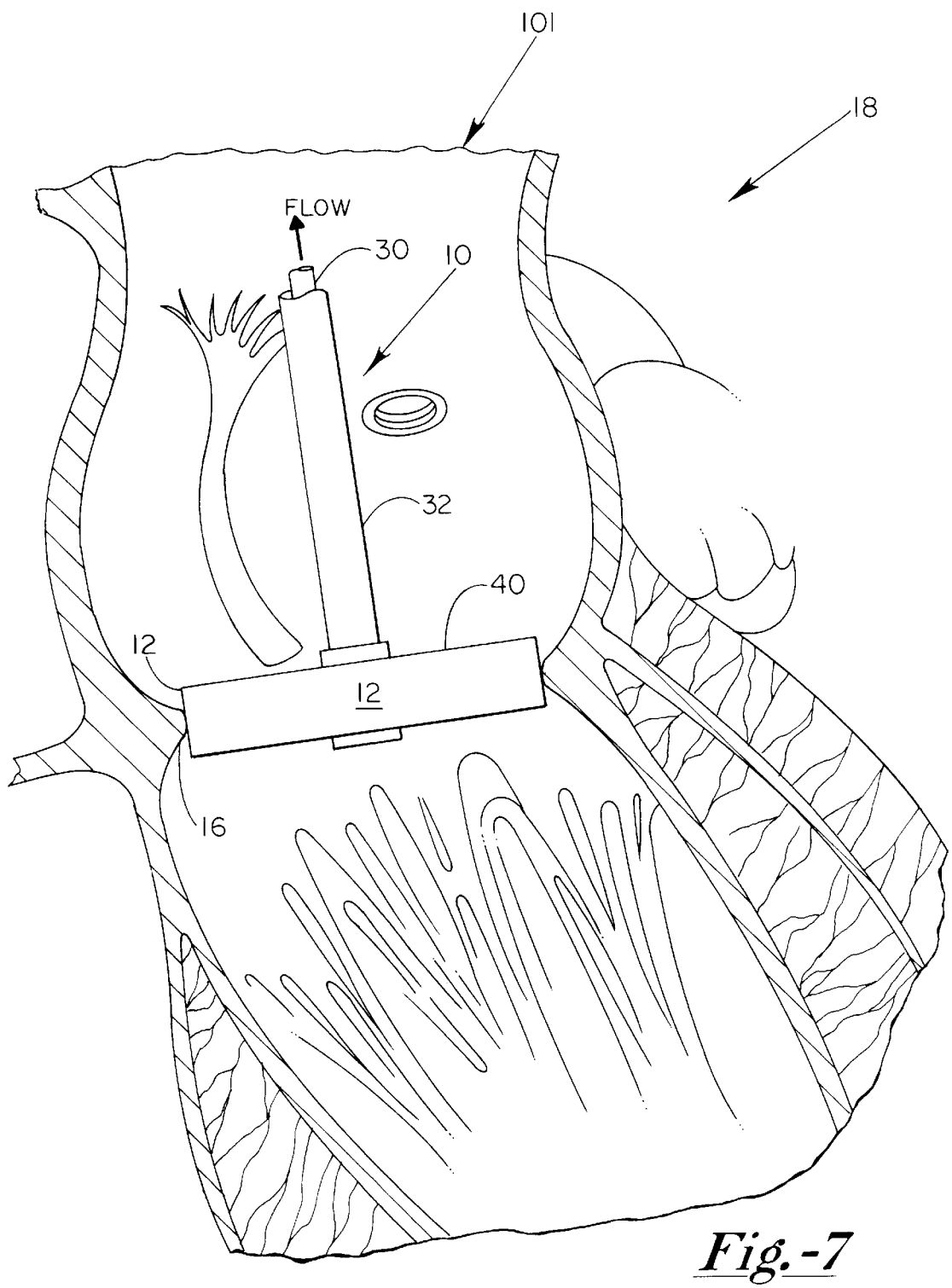
FIG. 7 is a side elevational view of a portion of the first embodiment of the present invention is use in a portion of a heart illustrated in section.

The outer surface 12 is disposed on a flexible band 40 that encircles the reference axis 14 and expands and contracts radially with respect to the reference axis 14 upon rotation of the gear 36. The flexible band 40 has a first end 42 secured to the housing 38 using suitable fasteners 44 such as rivets, bolts or screws. As appreciated by those skilled in the art, the first end 42 can be suitably glued or welded, or made integral with the housing 38, if desired. The flexible band 40 encircles the reference axis 14 and has a second free end 46 that slides upon an inner surface 48 of the flexible band 40. The flexible band 40 includes recesses 56 forming teeth 58 for engaging teeth 60 of the gear 36. Preferably, as illustrated in FIG. 3, each recess 56 does not extend completely through the flexible band 40, but rather, extends only part way through the thickness of the flexible band 40. In this manner, the outer surface 12 remains smooth so that the flexible band 40 slides freely within the inside diameter of the tissue annulus 16 (FIG. 7). The flexible band 40 can be formed from any suitable biocompatible material such as stainless steel, but preferably is made of a substantially clear plastic that allows viewing of the tissue annulus 16 through it.

The invention can be used for aortic and mitral sizing. For mitral sizing, segmented tags or extensions may be attached to rim 27 of adjustable member 26 shown in FIG. 1.

The operator actuated movable member 22 includes an adjusting knob 66 suitably secured to a proximal end of the rotating shaft 30, for example, by a set screw 67. Rotation of the adjusting knob 66 thereby rotates the shaft 30, which in turn rotates the gear 36 to displace an overlapping inner portion of the flexible band 40 relative to the outer portion having the outer surface 12. In the preferred embodiment, an indicator pointer 68 is located on the adjusting knob 66 and with rotation is selectively aligned with indicia 70 disposed on an annular member 72. The annular member 72 is secured to the outer casing 32.

In the preferred embodiment, rotation of the shaft 30 is selectively inhibited so that the adjustable member 26 periodically stops where the position of the outer curved surface 12 corresponds to available prosthetic heart valves. In one embodiment, as illustrated in FIG. 4, a detent mechanism 80 is provided between the adjusting knob 66 and the annular member 72. Specifically, the adjusting knob 66 includes a recess 82 formed on a lower surface 84 thereof. The recess 82 selectively engages spaced apart protrusions 86 formed on an upper surface 88 of the annular member 72. The protrusions 86 are angularly spaced apart about the shaft 30 so as to correspond to the indicia 70 provided on the annular member 72. Of course, if desired, the protrusions can be secured to the lower surface 84 of the adjusting knob 66 with the recess 82 or recesses provided on the upper surface 88.

Figure 4A:
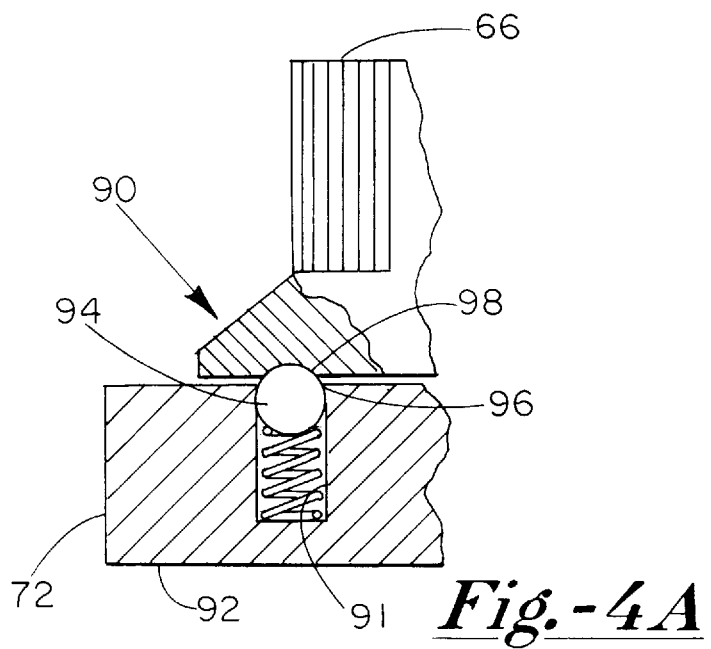
FIG. 4A is a sectional view of a second embodiment of a detent mechanism.
Figure 4:
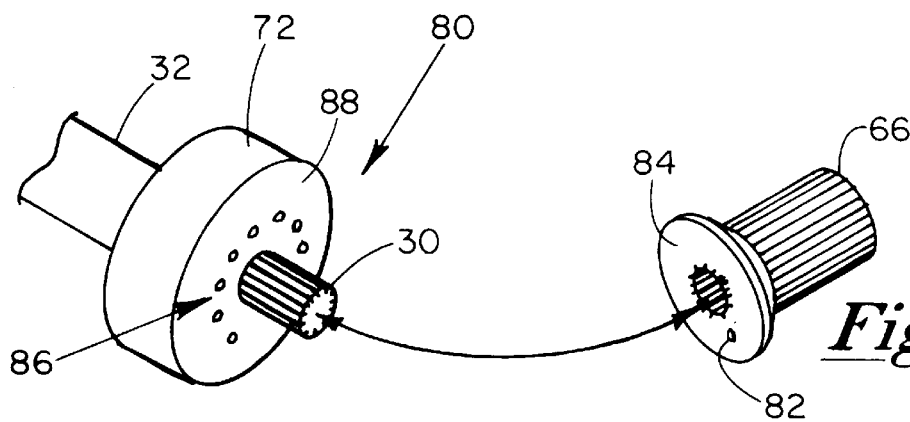
FIG. 4 is a partial exploded view of a first embodiment of a detent mechanism.

FIG. 4A illustrates a second detent mechanism 90. The detent mechanism 90 includes a spring 92 provided in a recess of the annular member 72. A ball 94 rests upon the spring 92 and protrudes through an aperture 96. A lower surface of the adjusting knob 66 includes a plurality of spaced apart recesses one of which is illustrated at 98. As the adjusting knob 66 rotates, the ball 94 periodically engages the recesses in the adjusting knob 66 to indicate when an available size of a prosthetic heart valve has been obtained.

Figure 5:
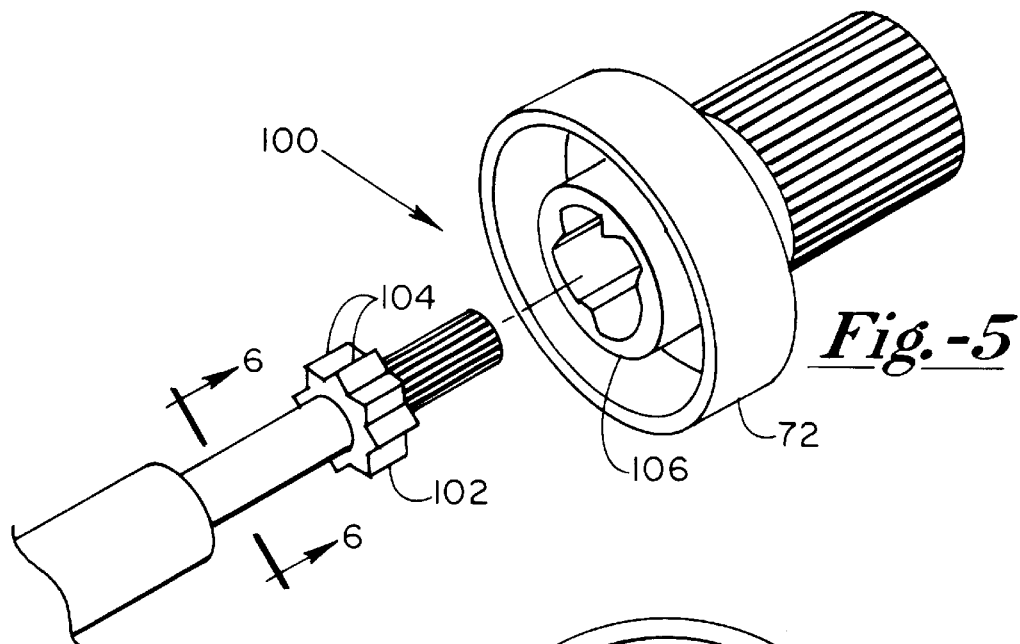
FIG. 5 is a partial exploded view of a third embodiment of a detent mechanism.
Figure 6:
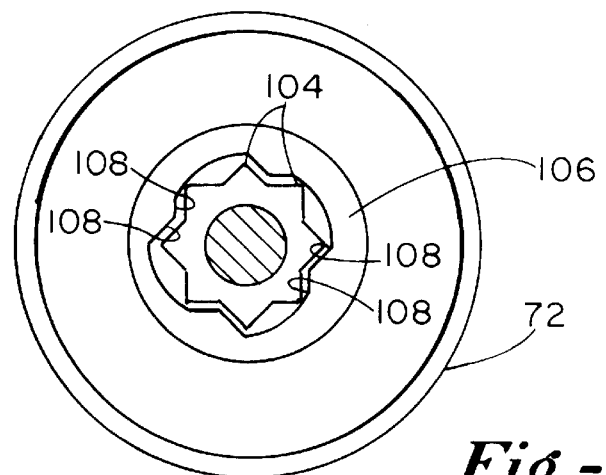
FIG. 6 is a sectional view taken along line 6—6 of FIG. 5.

A third embodiment of a detent mechanism 100 is illustrated in FIGS. 5 and 6. The detent mechanism 100 of this embodiment includes a gear 102 mounted to the shaft 30. The gear 102 is located within the annular member 72. The gear 102 includes a plurality of extending teeth 104. A flexible or compliant notched band 106 is mounted within the annular member 72 around or about the gear 102. As the gear 102 is rotated, the teeth 104 periodically engage inside stop surfaces 108 of the notched band 106. The detent mechanism 100 maintains substantially constant resistance during rotation with noticeable indications of an available prosthetic heart valve.

FIG. 8 illustrates a handle 120. The handle 120 is preferably made of plastic or metal, such as stainless steel, and joined to or made integral with the outer casing 32. If desired, the handle 120 can also be joined to or made integral with the annular member 72. Preferably, the shaft 30, the outer casing 32 and the handle 120 are flexible. The shaft 30 can be formed of plastic, Nitinol® (titanium/nickel alloy) or a flexible material or coupling, while the outer casing is formed of plastic, spiral wrapped plastic or spiral wrapped stainless steel. In the embodiment illustrated, the handle 120 includes annular groves 122 of sufficient depths to provide the attending physician with an easier grasp.

In operation, as illustrated in FIG. 7, the sizing apparatus 10 is positioned in a vessel 101 of the heart 18, preferably, with the native heart valve excised. The outer surface 12 of the adjustable member 26 is positioned within the inner diameter of the tissue annulus 16 of the heart 18. The adjusting knob 66 is rotated, moving past each indicia stop, until the outer surface 12 of the adjustable member 26 matches the inner diameter of the tissue annulus 16. The indicia 70 indicated on the annular member 72 will correspond to the prosthetic heart valve size to be implanted. This procedure applies to all embodiments discussed below, and applies to both aortic and mitral valves.

All components of the sizing apparatus 10, and the embodiments discussed below, can be formed from materials that withstand sterilizing procedures used in the medical industry.

FIG. 8A illustrates a second embodiment of a sizing apparatus 141 of the present invention suitable for sizing a tissue annulus to correspond with a prosthetic heart valve, not shown The sizing apparatus 141 includes the elongated support member 20 that couples the operator actuated movable member 22 to an adjustable member 143. The operator actuated movable member 22 is mounted to the proximal end 24 of the elongated support member 20, while the adjustable member 143 is mounted at the distal end 28 of the elongated support member 20.

The adjustable member 143 includes a drive assembly 145 having a rotatable drive element, preferably a gear 147, mounted to the shaft 30 for rotation therewith and a housing 149 (illustrated with dashed lines) for supporting the gear 147.

In this embodiment, an outer surface 151 is disposed on a flexible band 153 that encircles a reference axis 155 and expands and contracts radially with respect to the reference axis 155 upon rotation of the gear 147. The flexible band 153 has a first end 159 secured to the housing 149 (similar to the embodiment described above). The flexible band 153 encircles the reference axis 155 and has a second free end 165 that slides upon an outwardly facing surface of the flexible band 153. The flexible band 153 includes recesses 167 forming teeth for engaging corresponding teeth of the gear 147.

This embodiment is particularly useful in minimally invasive or thorascopic surgery, which is described in International Publication No. WO 94/18881, entitled METHOD FOR PERFORMING THORASCOPIC CARDIAC BYPASS PROCEDURES. In this procedure, elongated tools are used to operate on the heart through trocars. As discussed in Publication No. 94/18881, this procedure can be used during heart valve replacement The apparatus 143 can be inserted through the trocars to size the tissue annulus.

Figure 9:
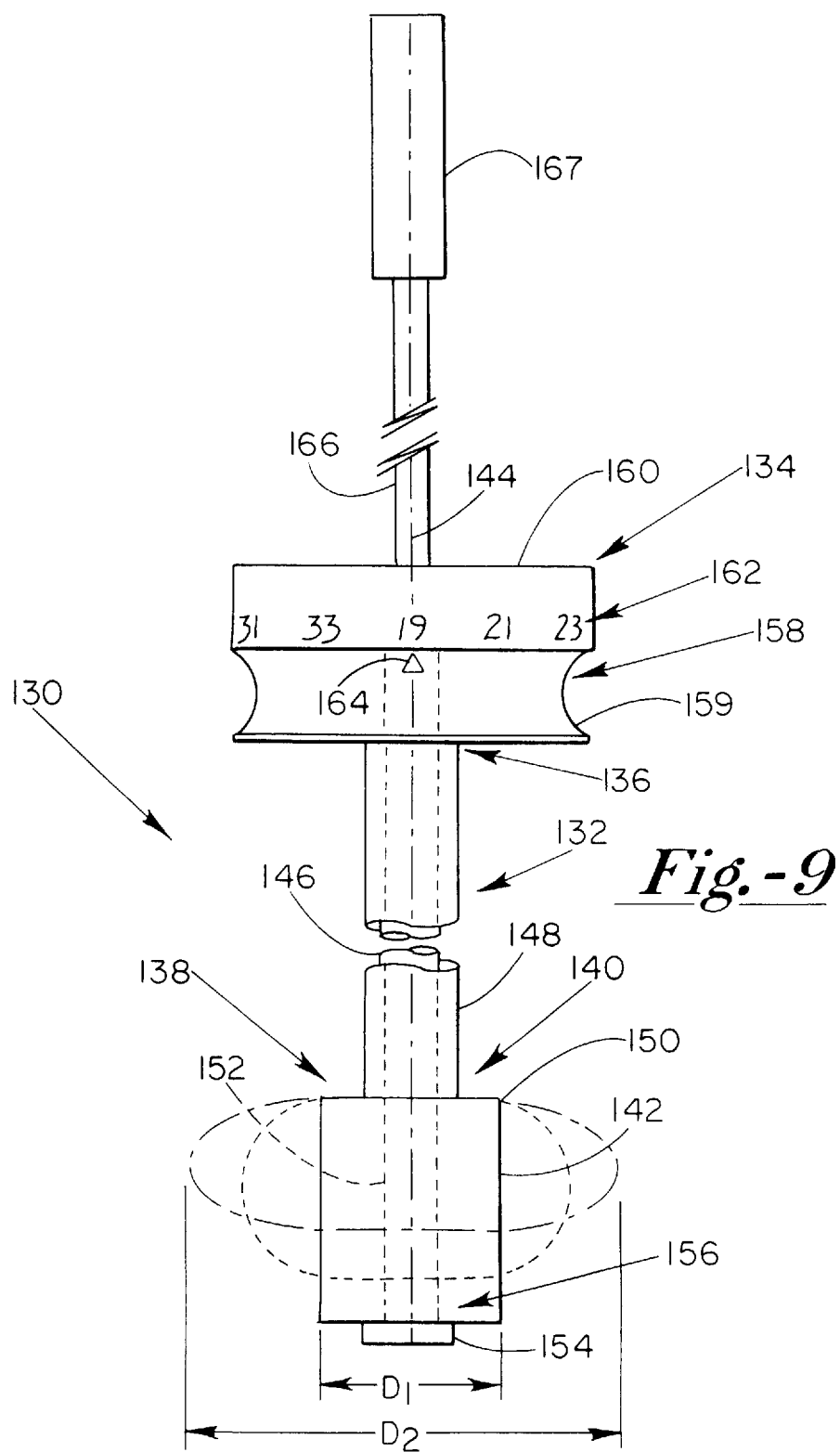
FIG. 9 is a front elevational view of a third embodiment of the present invention with parts broken away.

FIG. 9 illustrates a third embodiment of a sizing apparatus 130 of the present invention suitable for sizing a tissue annulus to correspond with a prosthetic heart valve, not shown. The sizing apparatus 130 includes an elongated support member 132 that couples an operator actuated movable member 134 to an adjustable member 138. The operator actuated movable member 134 is mounted to a proximal end 136 of the elongated support member 132, while the adjustable member 138 is mounted at a distal end 140 of the elongated support member 132. In particular, the adjustable member 138 responds to movements of the operator actuated movable member 134 so as to selectively displace an outer curved surface 142 toward or away from a reference axis 144.

The elongated support member 132 includes a shaft 146 that is rotatable within an outer support casing 148. The adjustable member 138 includes a compressible member 150 formed in a tube having a bore 152. The shaft 146 extends through the bore 152 and has a plate 154 joined to a distal end 156. An annular member 158 is joined to the outer casing 148 and includes a recess 159 to function as a handle. The annular member 158 and/or the outer casing 148 have threads which engage corresponding threads on the shaft 146. An adjusting knob 160 is joined to a proximal end of the shaft 146. Rotation of the adjusting knob 160 in a clockwise direction about the axis 144 pulls the plate 154 toward the annular member 158, which thereby compresses the compressible member 150 causing the outer surface 142 to be displaced outwardly from the reference axis 144. As illustrated, the compressible member 150 can be compressed through a range indicated by diameters $D_1$–$D_2$ When the adjusting knob 160 is rotated in a counter-clockwise direction, the compressible member 150 lengthens causing the outer surface 142 to displaced inwardly toward the reference axis 144. Suitable indicia 162 is disposed on the adjusting knob 160 and a indicator or pointer 164 is provided on the annular member 158. Any one of the detent mechanisms 80, 90 or 100 can be incorporated into the operator actuated movable member 134, as desired. If desired, a shaft 166 is joined to the shaft 146 and to a handle 167. The shaft 166 is preferably flexible so as to allow the adjustable member 138 to be positioned proximate the tissue annulus 16 illustrated in FIG. 7.

FIGS. 10 and 11 illustrate a fourth embodiment of a sizing apparatus 180 of the present invention suitable for sizing a tissue annulus to correspond with a prosthetic heart valve, not shown. The sizing apparatus 180 includes an elongated support member 182 that couples an operator actuated movable member 184 to an adjustable member 188. The operator actuated movable member 184 is mounted to a proximal end 186 of the elongated support member 182, while the adjustable member 188 is mounted at a distal end 190 of the elongated support member 182. In particular, the adjustable member 188 responds to movements of the operator actuated movable member 184 so as to selectively displace an outer curved surface 192 toward or away from a reference axis 194.

The elongated support member 182 includes a shaft 196 that is rotatable within an outer support casing 198. The adjustable member 188 includes a flexible band 200 that encircles the reference axis 194 and expands and contracts radially with respect to the reference axis 194 with rotation of the shaft 196. The flexible band 200 has a first end 202 suitably fastened to a drive lever or arm 204 that is mounted to a distal end of the shaft 196 for rotation therewith. A second end 206 of the flexible band 200 is mounted to a strut 208. The strut 208 is secured to and pivots on a support block 210 joined to the outer casing 198. Although illustrated with a suitable pivot pin 212, if the strut 208 is suitably flexible, the pivot pin 212 can be eliminated.

The operator actuated movable member 184 includes an adjusting knob 218 joined to a proximal end 186 of the rotatable shaft 196. An annular member 220 functions as a handle and is secured to the outer casing 198. Rotation of the adjusting knob 218, the shaft 196 and the drive arm 204 in a clockwise direction, indicated by arrow 195 in FIG. 11, causes the flexible band 200 to expand. When the adjusting knob 218, shaft 196 and drive arm 204 are rotated in a counter-clockwise direction as viewed in FIG. 11, the flexible band 200 contracts. Preferably, the flexible band 200 is formed metal such as stainless steel or clear plastic and wound to provide a constant force spring, which tends to return to its smallest diameter. Any one of the detent mechanisms 80, 90 or 100 described above can be incorporated into the operator actuated movable member 184, as desired. Suitable indicia 222 are disposed on the adjusting knob 218 and together with a pointer 224 provided on the annular member 220 indicate the correct prosthetic heart valve to use.

FIGS. 12 and 13 illustrate a fifth embodiment of a sizing apparatus 240 of the present invention suitable for sizing a tissue annulus to correspond with a prosthetic heart valve, not shown. The sizing apparatus 240 includes an elongated support member 242 that couples an operator actuated movable member 244 to an adjustable member 248 The operator actuated movable member 244 is mounted to a proximal end 246 of the elongated support member 242, while the adjustable member 248 is mounted to a distal end 250 of the elongated support member 242. The adjustable member 248 responds to movements of the operator actuated movable member 244 so as to selectively displace outer curved surface portions 252 toward or away from a reference axis 254.

The elongated support member 242 includes a shaft 256 that is rotatable within an outer support casing 258. The adjustable member 248 includes a cone-shaped drive member 260 mounted to a distal end of the shaft 256. The adjustable member 248 further includes a support base 262 secured to the outer casing 258. The support base 262 includes an aperture 264 allowing the shaft 256 to extend therethrough. A plurality of extending arms 266 are joined to a lower surface 268 of the support base 262. Preferably, the extending arms 266 are joined to the support base 262 at equal angular intervals about the reference axis 254. In the embodiment illustrated, four depending arms 266 are illustrated; however, if desired, any number of arms can be used. A drive block 270 is mounted to a lower portion of each arm 266 and extends inwardly toward the reference axis 254. As illustrated in FIG. 13, a portion of the outer curved surface 252 is mounted to each drive block 270 and faces outwardly.

An adjusting knob 280 is joined to a proximal end 246 of the rotatable shaft 256. The rotatable shaft 256 extends through a suitable aperture 257 in an annular member 282 that functions as a handle and is secured to the outer casing 258. The shaft 256 includes threads which engage at least one of the support base 262, the outer casing 258 or the annular member 282. Rotation of the adjusting knob 280 rotates the shaft 256 which in turn rotates and displaces the cone-shaped drive member 260 about and along the reference axis 254. An outer surface 284 of the cone-shaped drive member 260 contacts the drive blocks 270 to displace them outwardly. Preferably, the arms 266 are made of a suitable compliant material such as clear plastic so that with movement of the cone-shaped drive member 260 toward the support base 262, the outer surface portions 252 are returned to their position as illustrated in FIG. 13. Any one of the detent mechanisms 80, 90 or 100 described above can be incorporated into the operator actuated movable member 244, as desired. Suitable indicia 290 and a pointer 292 are provided on the adjusting knob 280 and the annular member 282, respectively, to indicate available prosthetic heart valves.

Figure 14:
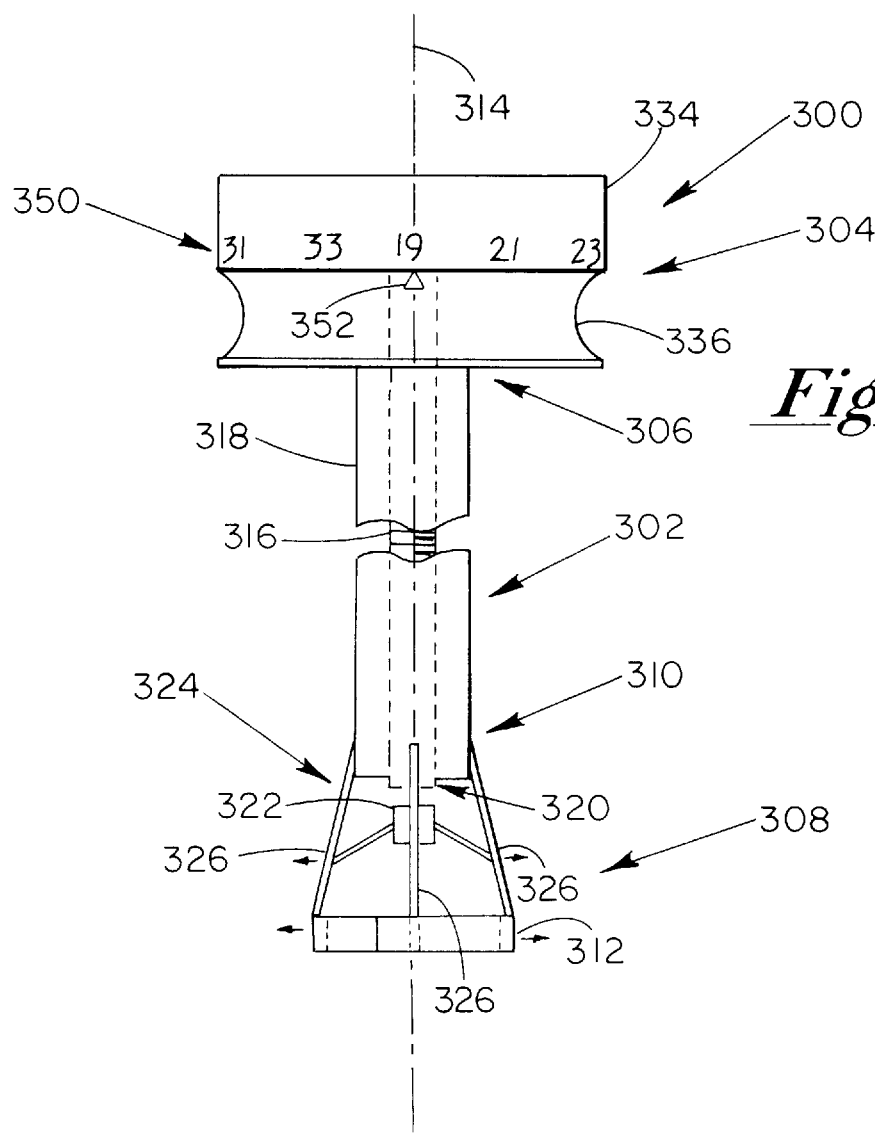
FIG. 14 is a side elevational view of a sixth embodiment of the present invention with a portion broken away.
Figure 15:
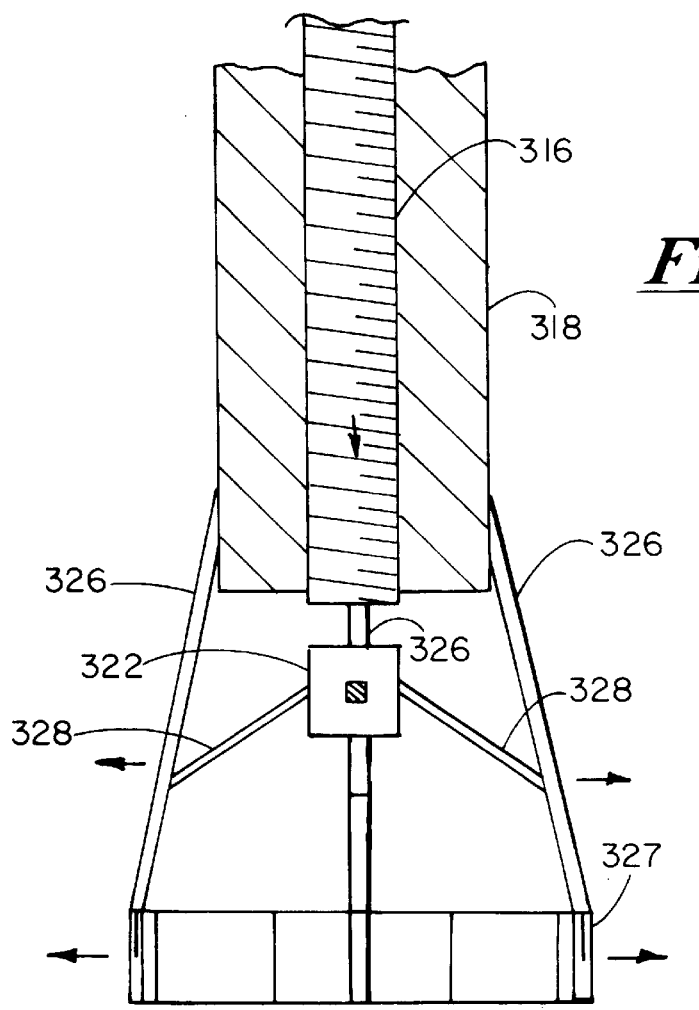
FIG. 15 is an enlarged sectional view of the sixth embodiment.
Figure 16:
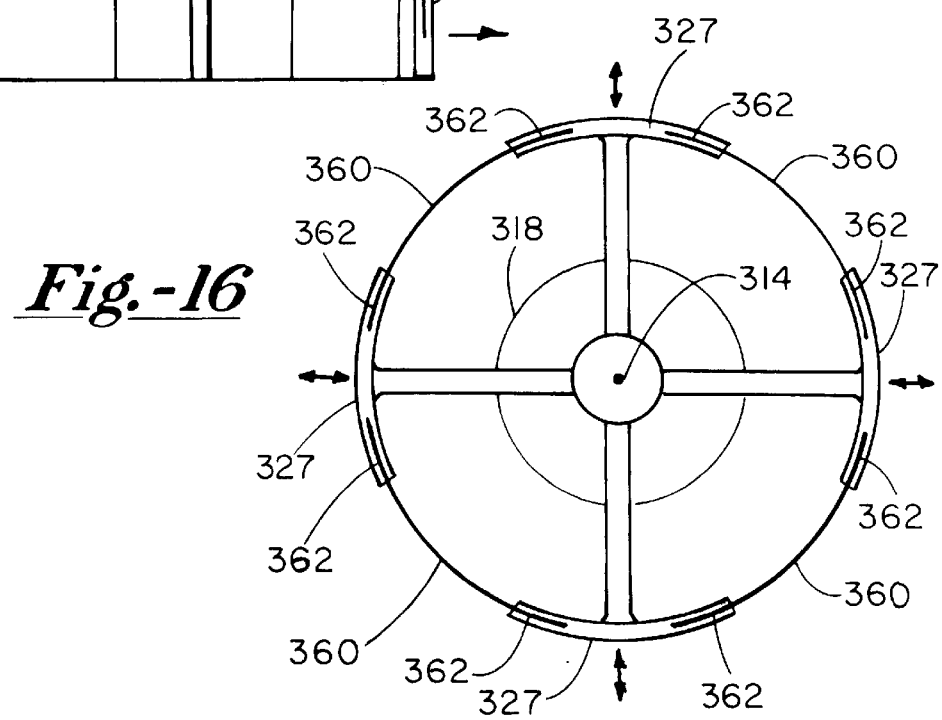
FIG. 16 is a bottom plan view of movable elements of the sixth embodiment.

FIGS. 14, 15 and 16 illustrate a sixth embodiment of a sizing apparatus 300 of the present invention suitable for sizing a tissue annulus to correspond with a prosthetic heart valve, not shown. The sizing apparatus 300 includes an elongated support member 302 that couples an operator actuated movable member 304 to an adjustable member 308. The operator actuated movable member 304 is mounted to a proximal end 306 of the elongated support member 302, while the adjustable member 308 is mounted to a distal end 310 of the elongated support member 302. The adjustable member 308 responds to movements of the operator actuated movable member 304 so as to selectively displace outer curved surface portions 312 toward or away from a reference axis 314.

The elongated support member 302 includes a shaft 316 that is rotatable within an outer support casing 318. A distal end 320 of the shaft 316 engages a drive member 322 of the adjustable member 308. The adjustable member 308 further includes a hinge assembly 324 connected to the outer support casing 318 and the drive member 322. The hinge assembly 324 includes a plurality of extending arms 326 having a first end joined to the outer support casing 318. At a distal end of each arm 326, a curved plate 327 is mounted. Each of the curved plates 327 include a portion of the outer curved surface 312. A drive strut 328 is connected to the drive member 322 and extends outwardly to connect to each of the extending arms 326. As illustrated in FIG. 15, the drive struts 328 support the drive member 322 below the shaft 316.

Referring back to FIG. 14, an adjusting knob 334 is joined to a proximal end of the shaft 316. The shaft 316 extends through a suitable aperture in an annular member 336 that functions as a handle and is secured to the outer casing 318. Preferably, the shaft 316 includes threads which engage the outer casing 318 or the annular member 336. Rotation of the adjusting knob 334 rotates the shaft 316 which in turn causes the distal end 320 to engage the drive member 322. As the drive member 322 is pushed downwardly along the reference axis 314, the drive struts 328 push each of the extending arms 326 outwardly. Preferably, the arms 326 are joined to the outer casing 318 at equal angular intervals about the reference axis 314. In the embodiment illustrated, four arms 326 are illustrated; however, if desired, any number of arms can be used. The arms 326 and the struts are made of a suitable compliant material such as plastic so that with movement of the drive member 322 upwardly toward the annular member 336, the outer curved surface portions 312 are returned to their position closest to the reference axis 314. If desired, hinge pins, not shown, can be used to pivotally join the struts 328 to the outer casing 318 and the arms 326, as well as the arms 326 to the outer casing 318. Any one of the detent mechanisms 80, 90 or 100 described above can be incorporated into the operator actuated movable member 304, as desired. Suitable indicia 350 and a pointer 352 are provided on the adjusting knob 334 and the annular member 336, respectively, to indicate available prosthetic heart valves.

Referring to FIG. 16, if desired, flexible band elements 360 made of clear plastic or stainless steel interconnect each of the plates 327. As illustrated, the plates 327 include suitable slots 362 that receive ends of the band elements 360. The ends of the band elements 360 slide in the slots 362 as the plate portions 327 are displaced inwardly and outwardly with respect to the reference axis 314.

Figure 17:
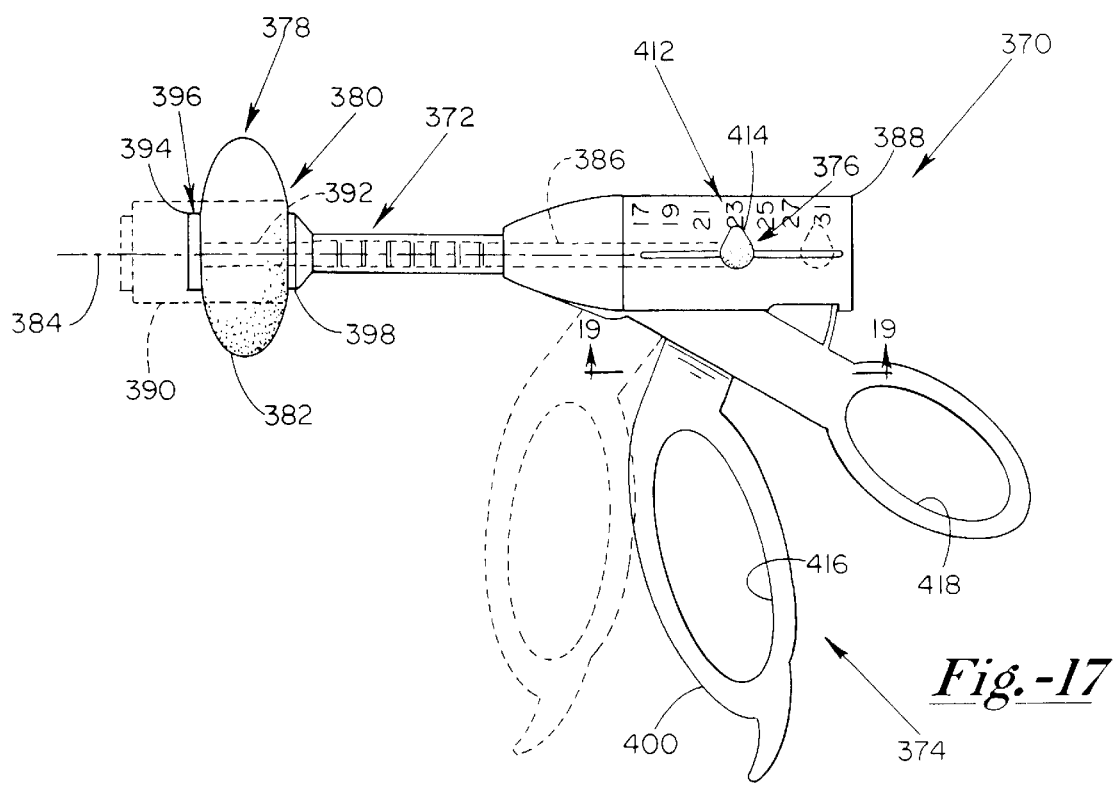
FIG. 17 is a side elevational view of a seventh embodiment of the present invention.
Figure 18:
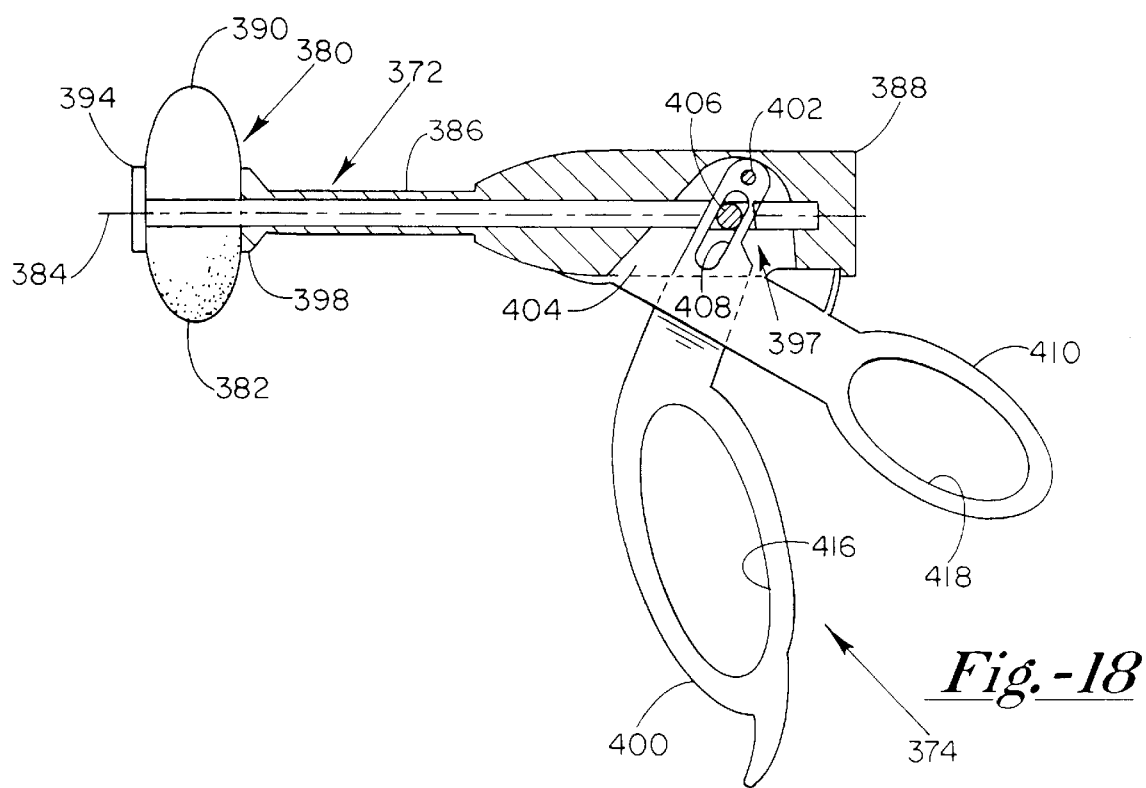
FIG. 18 is a sectional view of the seventh embodiment.
Figure 19:
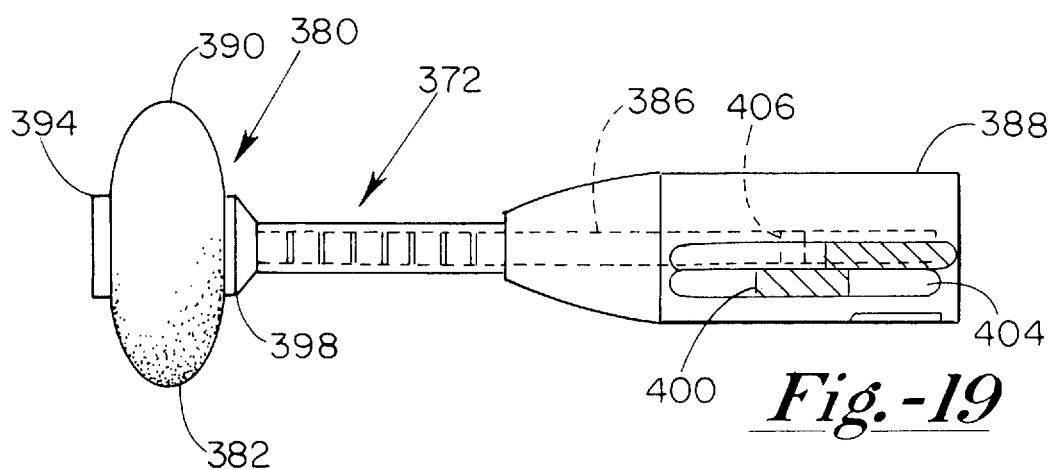
FIG. 19 is a sectional view of the seventh embodiment taken along line 19—19 in FIG. 17.

FIGS. 17–19 illustrate a seventh embodiment of a sizing apparatus 370 of the present invention suitable for sizing a tissue annulus to correspond with, for instance, a prosthetic heart valve, not shown. The sizing apparatus 370 includes an elongated support member 372 that couples an operator actuated movable member 374 to an adjustable member 378. The operator actuated movable member 374 is mounted to a proximal end 376 of the elongated support member 372, while the adjustable member 378 is mounted at a distal end 380 of the elongated support member 372. In particular, the adjustable member 378 responds to movements of the operator actuated movable member 374 so as to selectively displace an outer curved surface 382 toward or away from a reference axis 384.

The elongated support member 372 includes a shaft 386 that is slidable within an outer support casing 388. The adjustable member 378 includes a compressible member 390 formed in a tube (shown with dashed lines) having a bore 392. The compressible member 390 can be extended or compressed as shown in FIG. 17. The shaft 386 extends through the bore 392. A plate 394 is joined to a distal end 396 of the shaft 386.

Referring to FIG. 18, a proximal end 397 of the shaft 386 is coupled to the operator actuated movable member 374. In the embodiment illustrated, the operator actuated movable member 374 includes a lever 400 that is pivotally joined to the outer support casing 388 with a pin 402. The lever 400 extends within a recess 404 of the outer support casing 388. The proximal end 397 of the shaft 386 is coupled to the lever 400 with a pin 406. The pin 406 extends into a longitudinal slot 408 formed in the lever 400. Pivotal movement of the lever 400 on the outer support casing 388, with respect to a fixed support 410, pulls the plate 394 toward an annular member 398; which thereby compresses the compressible member 390, causing the outer curved surface 382 to be displaced outwardly from the reference axis 384. The compressible member 390 can be compressed through a range of diameters similar to the third embodiment illustrated in FIG. 9. As shown in FIG. 17, a pointer 414 is coupled to the shaft 386 and moves adjacent indicia 412 provided on the casing 388 to indicate available prosthetic heart valves. Apertures 416 and 418 are provided in the lever 400 and the fixed support 410, respectively, to receive fingers and a thumb of the operator's hand.

Figure 20:
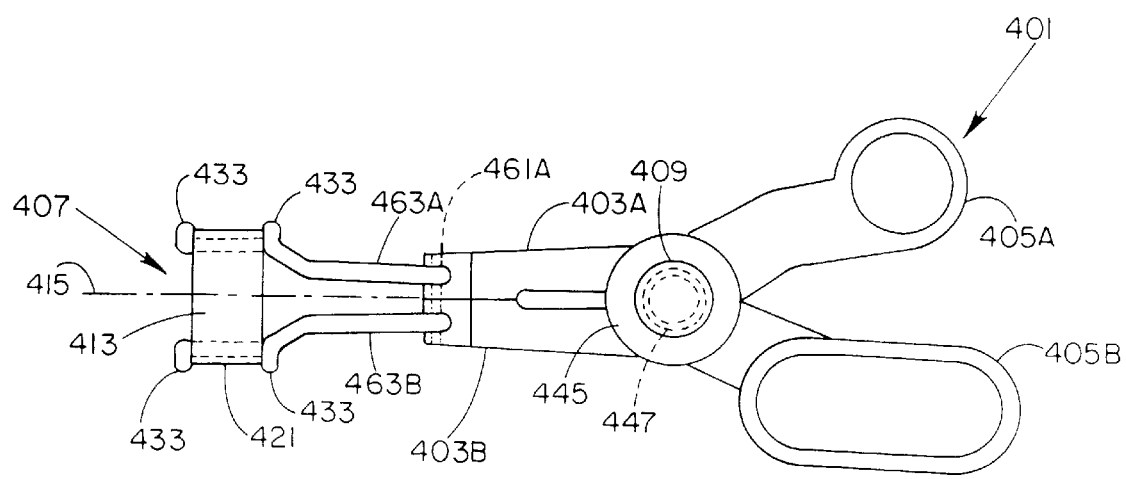
FIG. 20 is a side elevational view of an eighth embodiment of the present invention in a first position.
Figure 21:
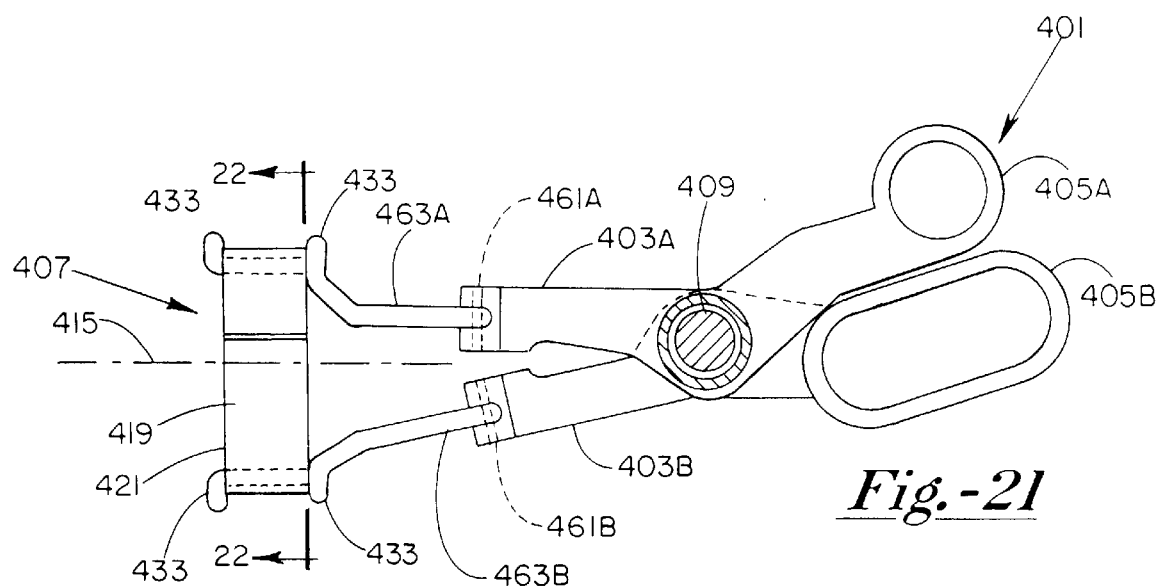
FIG. 21 is a side elevational view of the eighth embodiment in a second position and with a portion broken away.

FIGS. 20 and 21 illustrate an eighth embodiment of a sizing apparatus 401 of the present invention suitable for sizing the tissue annulus. The sizing apparatus 401 includes elongated support members 403A and 403B that pivot with respect to each other about a pin 409. Preferably, each of the elongated support members 403A and 403B includes extending handles 405A and 405B, respectively. An adjustable member 407 is mounted at distal ends of the elongated support members 403A and 403B. The adjustable member 407 responds to pivotal movements of the elongated support members 403A and 403B so as to selectively displace an outer curved surface 413 toward or away from a reference axis 415.

Figure 22:
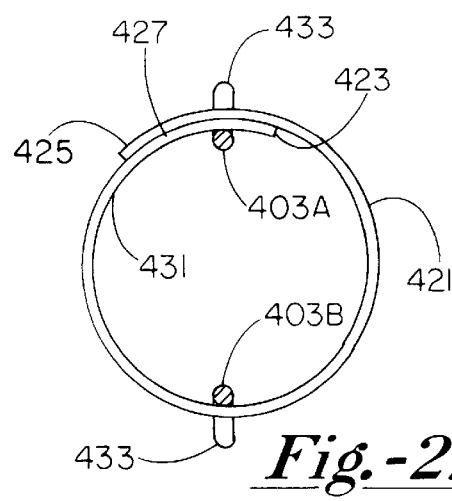
FIG. 22 is a sectional view of the eighth embodiment taken along line 22—22 in FIG. 21.

Referring also to FIG. 22, the adjustable member 407 comprises a flexible band 421 that encircles the reference axis 415 and expands and contracts radially with respect to the reference axis 415 with pivotal movements of the elongated support members 403A and 403B about the pin 409. The flexible band 421 has a first end 423 and a second end 425 that overlaps and slides upon a surface 427 of the first end 423 The elongated support members 403A and 403B are in contact and slide upon an inner surface 431 of the flexible band 421. The flexible band 421 forms a spring which wants to collapse to its smallest diameter as illustrated in FIG. 20. With pivotal movement of the elongated support members 403A and 403B away from each other, the elongated support members 403A and 403B expand the flexible band 421, while the overlapping portion of the second end 425 remains in contact with the surface 427 to substantially form a circle. Posts 433 secured to the elongated support members 403A and 403B on opposite side edges of the flexible band 421 retain the flexible band 421 on the elongated support members 403A and 403B.

Figure 21A:
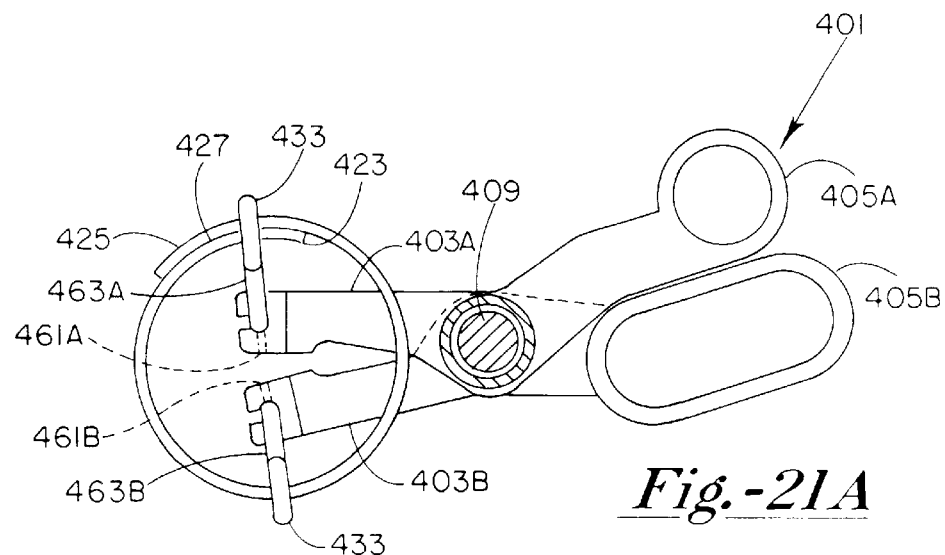
FIG. 21A is a side elevational view of the eighth embodiment in a third position and with a portion broken away.

In the embodiment illustrated, the elongated support members 403A and 403B include pivot pins 461A and 461B, which allow the adjustable member 407 to be positioned as shown in FIG. 21A. In particular, the pivot pins 461A and 461B allow portions 463A and 463B of the support members 403A and 403B, respectively, to be placed perpendicular to a plane of motion of handles 405A and 405B, or parallel to pin 409. In this position, the distal ends of the portions 463A and 463B, supporting the flexible band 421, move substantially in a straight line with angular displacements of the support members 403A and 403B.

Figure 23:
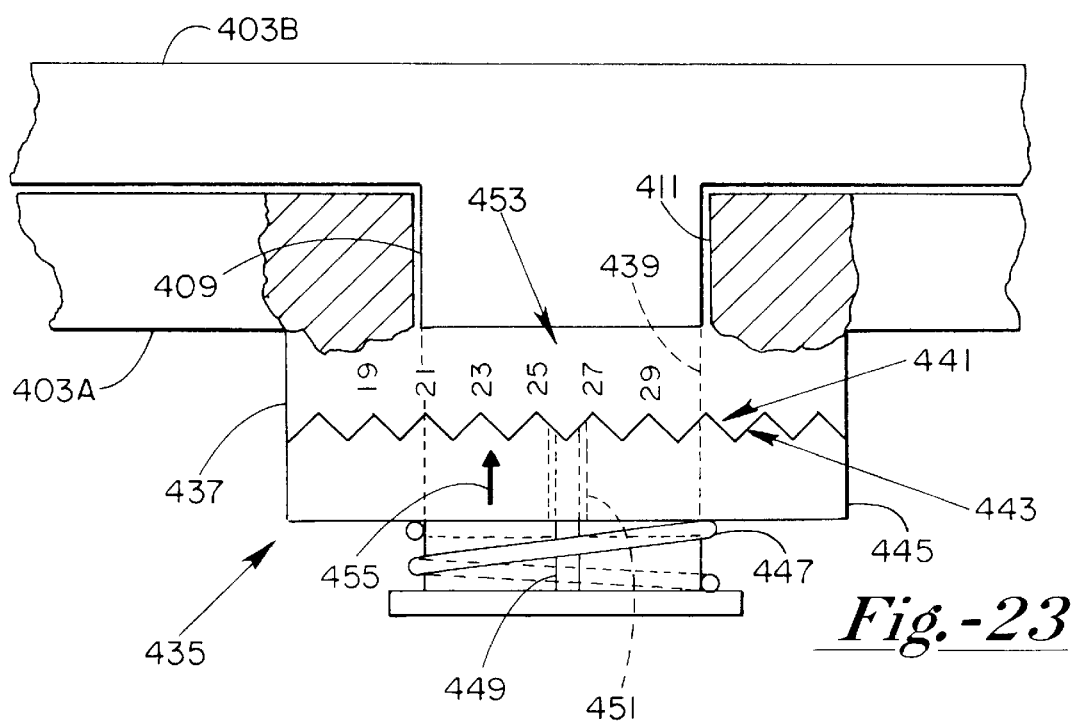
FIG. 23 is an enlarged top plan view of a portion of the eighth embodiment with a portion broken away.
Figure 24:
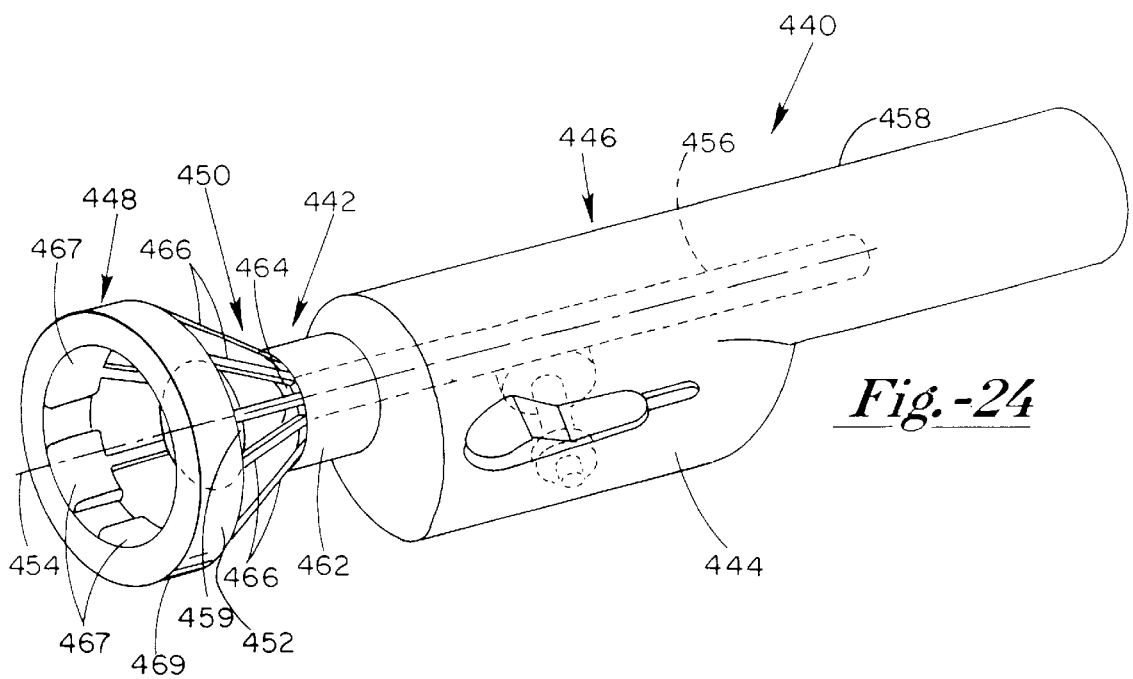
FIG. 24 is a perspective view of a ninth embodiment of the present invention.

Referring to FIG. 23, the pin 409 is secured to the elongated support member 403B and extends through an aperture 411 in the elongated support member 403A. A rachet assembly 435 is mounted to the pin 409. The rachet assembly 435 controls pivotal displacement of the elongated support members 403A and 403B so that the diameter of the adjustable member 407 corresponds to available prosthetic heart valves. The rachet assembly 435 includes a first disk 437 secured to the elongated support member 403A. The disk 437 includes an aperture 439 through which the pin 409 extends. The disk 437 includes teeth 441 that engage teeth 443 of a second disk 445. The second disk 445 is biased toward the disk 437 by a spring 447. As the elongated support members 403A and 403B pivot with respect to each other, the disk 437 pivots about the pin 409. The disk 445 does not rotate about the pin 409, but rather, slides axially on the pin as the teeth 441 and 443 engage and disengage. A rib 449 formed on the pin 409 extends into a notch 451 provided in the disk 445 to prevent rotational movement of the disk 445 about the pin 409. Indicia 453 provided on the disk 437 and a pointer 455 on the disk 445 indicates available sizes of prosthetic heart valves.

FIGS. 24–27 illustrate a ninth embodiment of a sizing apparatus 440 of the present invention suitable for sizing a tissue annulus, such as a prosthetic heart valve, not shown. The sizing apparatus 440 includes an elongated support member 442 that couples an operator actuated movable member 444 to an adjustable member 448. The operated actuated movable member 444 is mounted at a proximal end 446 of the elongated support member 442, while the adjustable member 448 is mounted to a distal end 450 of the elongated support member 442. The adjustable member 448 responds to movements of the operator actuated movable member 444 so as to selectively displace an outer curved surface 452 toward or away from a reference axis 454.

The elongated support member 442 includes a shaft 456 that is slidable within an outer support casing 458. A cone-shaped drive member 459 is mounted to a distal end of the shaft 456. The elongated support member 442 further includes a support base 462 secured to the outer support casing 458. The support base 462 includes an aperture 464 allowing the shaft 456 to extend out of the outer support casing 458. A plurality of extending arms 466 are joined to the support base 462. Preferably, the plurality of extending arms 466 are joined to the support base 462 at equal angular intervals about the reference axis 454. Each extending arm 466 includes an end portion 467. Preferably, a clear, flexible band 469 encircles the reference axis 454 and is supported by each of the end portions 467.

Figure 25:
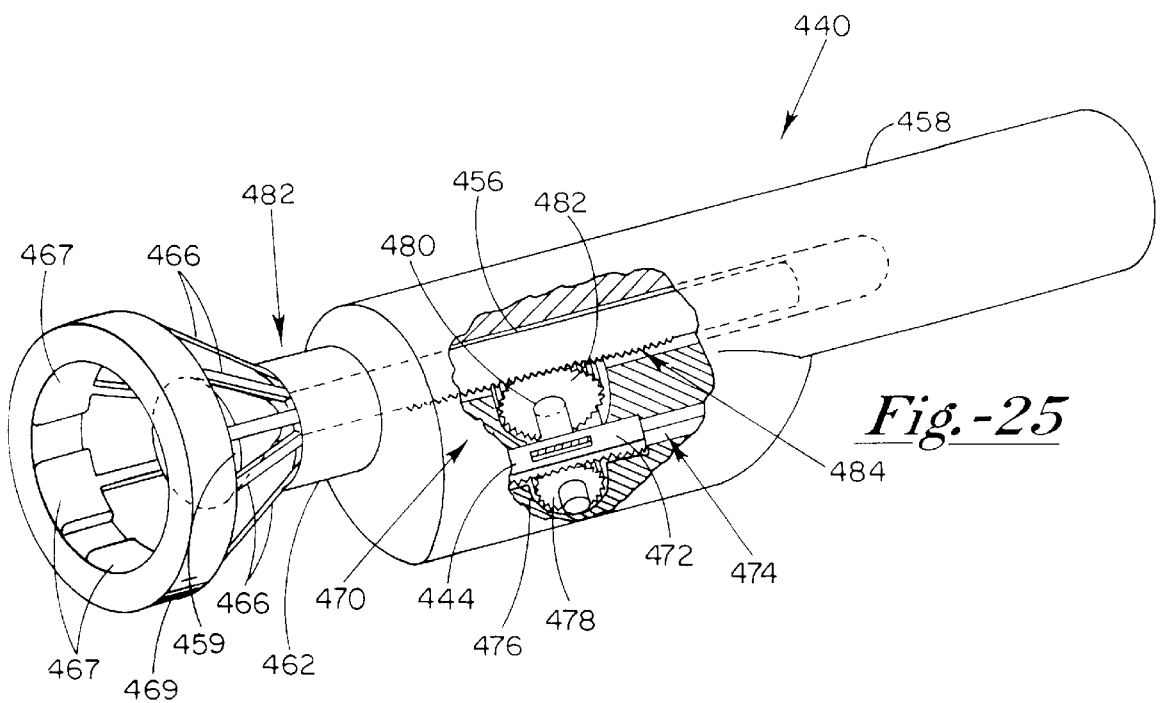
FIG. 25 is a perspective view of the ninth embodiment with a portion of a housing broken away.
Figure 26:
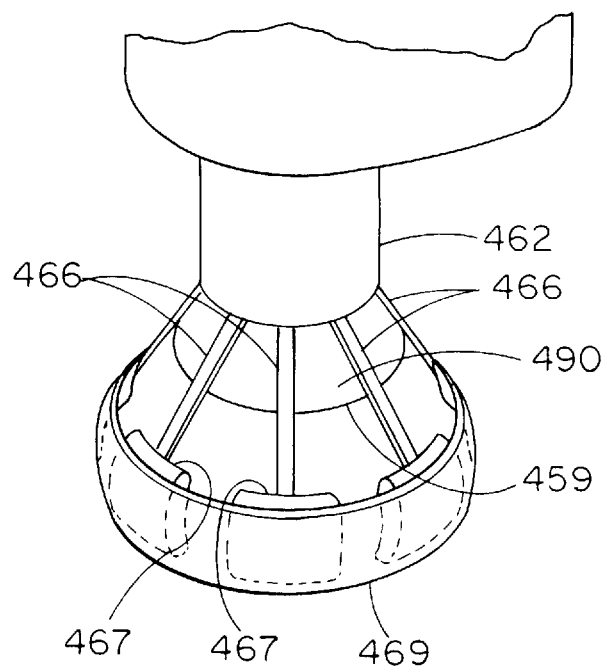
FIG. 26 is an enlarged perspective view of a portion of the ninth embodiment.
Figure 27:
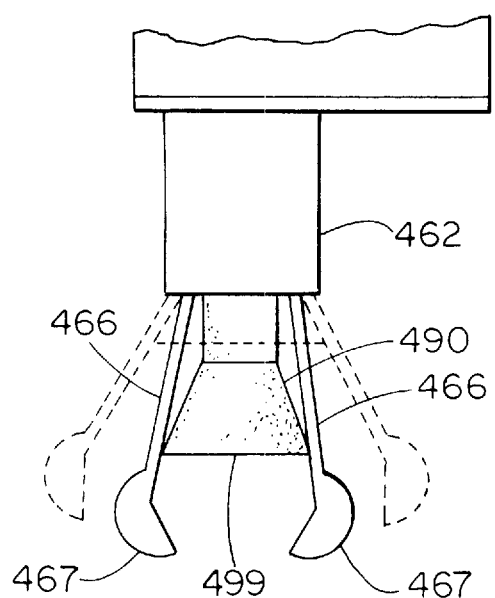
FIG. 27 is a diagrammatic view of movable elements of the ninth embodiment.

Referring to FIG. 25, the operator actuated movable member 444 displaces the shaft 456 through a gear assembly 470. A drive plate 472 slidably displaced in a channel 474 includes teeth 476 that engage teeth on a gear 478. A drive shaft 480 couples the gear 478 to a gear 482. Linearly disposed teeth 484 provided on the shaft 456 engage teeth on the gear 482. Although illustrated where a diameter of the gear 482 is larger than a diameter of the gear 478, it should be understood that the gears 478 and 482 can have the same diameter, or the gear 478 can have a larger diameter than the gear 482. Sliding displacement of the drive plate 472 rotates the gear 478, which in turn, rotates the gear 482 to linearly displace the shaft 456 and the cone-shaped drive member 459 along the reference axis 454. An outer surface 490 of the cone-shaped drive member 459 contacts the plurality of extending arms 466 to displace them outwardly, as shown in FIG. 27.

Figure 28:
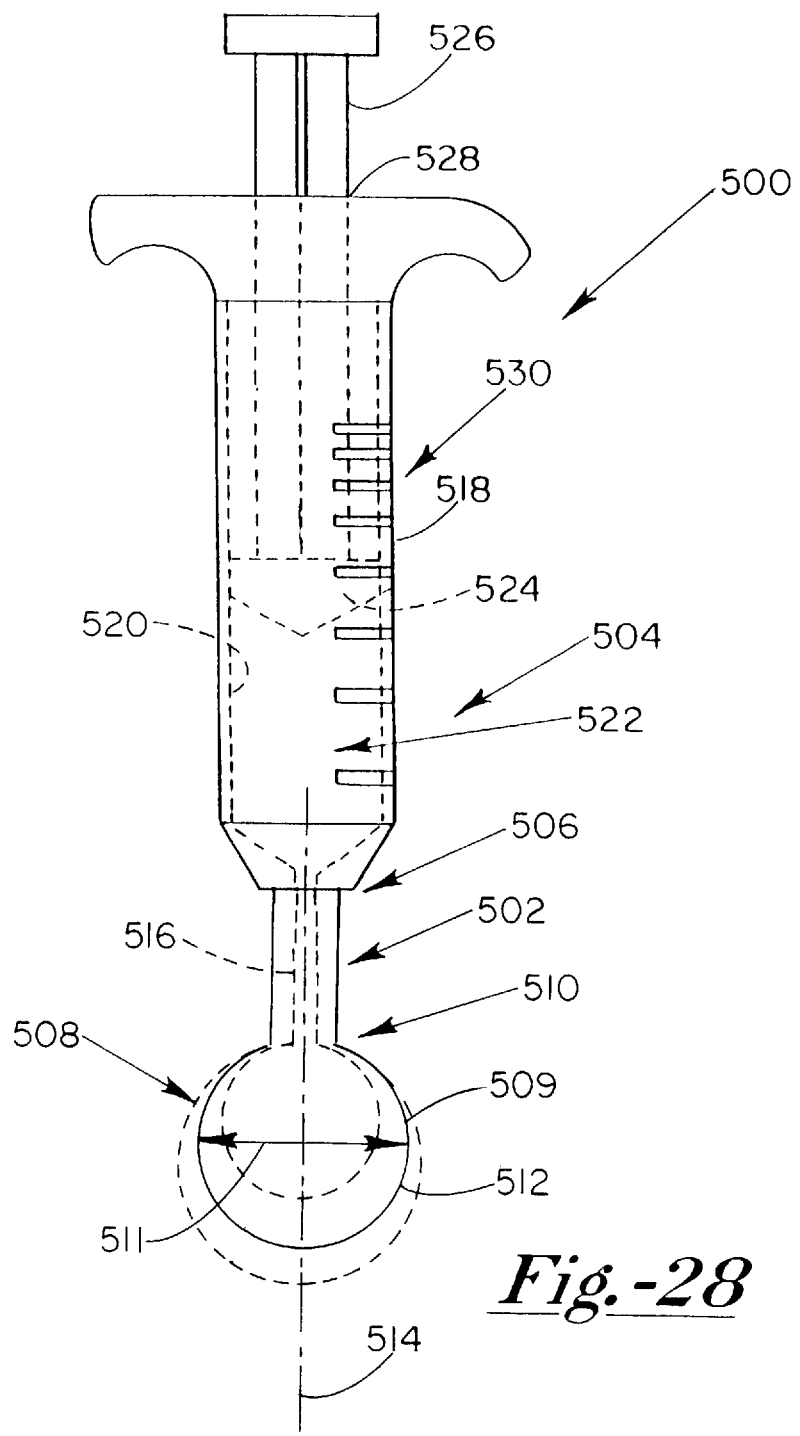
FIG. 28 is a side elevational view of a tenth embodiment of the present invention.

FIG. 28 illustrates a tenth embodiment of a sizing apparatus 500 of the present invention suitable for sizing a tissue annulus for implantation of a prosthetic heart valve, not shown. The sizing apparatus 500 includes an elongated support member 502 that couples an operator actuated movable member 504 to an adjustable member 508. The operator actuated movable member 504 is mounted to a proximal end 506 of the elongated support member 502, while the adjustable member 508 is mounted on a distal end 510 of the elongated support member 502. In particular, the adjustable member 508 responds to movements of the operator actuated movable member 504 so as to selectively displace an outer curved surface 512 toward or away from a reference axis 514.

In this embodiment, the adjustable member 508 is an expandable member such as an inflatable balloon 509. The elongated support member 502 includes a passageway 516 that fluidly couples the adjustable member 508 to the operator actuated movable member 504, comprising a pump for filling the balloon 509. The fluid used to fill the balloon 509 can be either a compressible fluid, such as air, or, a less compressible fluid, such as sterilized water. A particular advantage of the balloon 509 is that it can also form a plug to seal the tissue annulus to prevent excised tissue or other material from passing through the tissue annulus. The compressible members 150 and 390 of the previous embodiments can also form a plug to seal the tissue annulus if desired.

The operator actuated movable member 504 includes an outer housing 518 having an inner wall 520 forming a cylindrical chamber 522. A piston 524 slides within the chamber 522 on the inner wall 520 to control fluid flow through the passageway 516 in order to inflate or deflate the balloon 509. A connecting rod 526 is joined to the piston 524 and extends out through a suitable aperture 528 on an end of the outer housing 518. An operator controls the position of the piston 524 within the chamber 522 by applying a suitable force to the end of the connecting rod 526.

The outer housing 518 can be transparent so that a position of the piston 524 within the chamber 522 can be observed. The position of the piston 524 within the chamber 522 corresponds to a diameter (indicated by double arrow 511) of the balloon 509. Suitable indicia 530 provided on the outer housing 518 proximate the piston 524 indicates various sizes the diameter of the inflated balloons, which can correspond with prosthetic heart valves.

This embodiment is also particularly useful in minimally invasive or thorascopic surgery since the balloon 509 can be deflated allowing it and the support member 502 to be passed though a trocar, expanded for sizing, and then deflated for removal.

Figure 29:
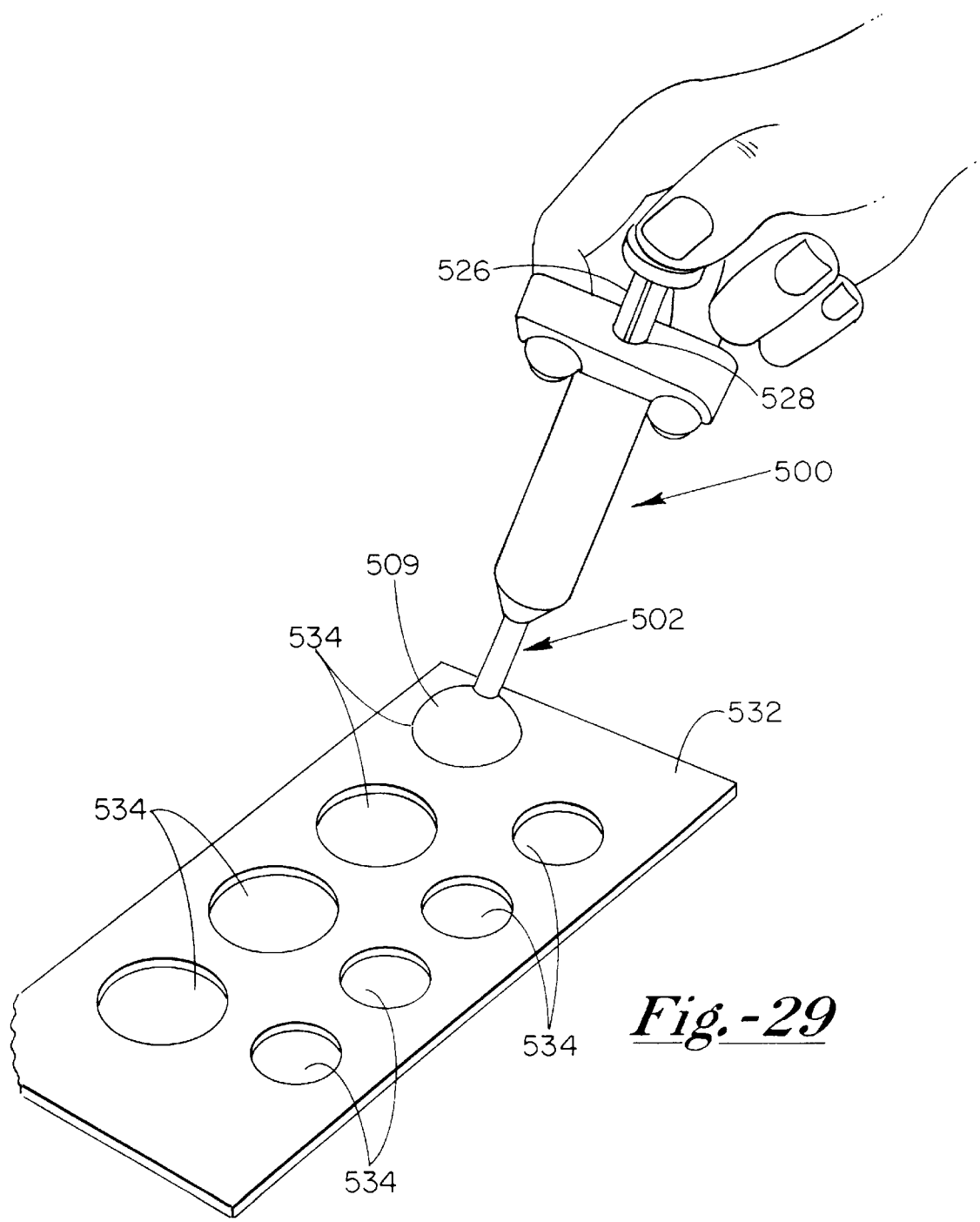
FIG. 29 is a perspective view of the tenth embodiment and a sizing plate.

FIG. 29 illustrates a plate 532 for indicating the size of the balloon 509 after inflation. The plate 532 includes apertures 534 of different size corresponding to the anatomical feature to be measured such as the tissue annulus for a prosthetic heart valve.

Figure 30:
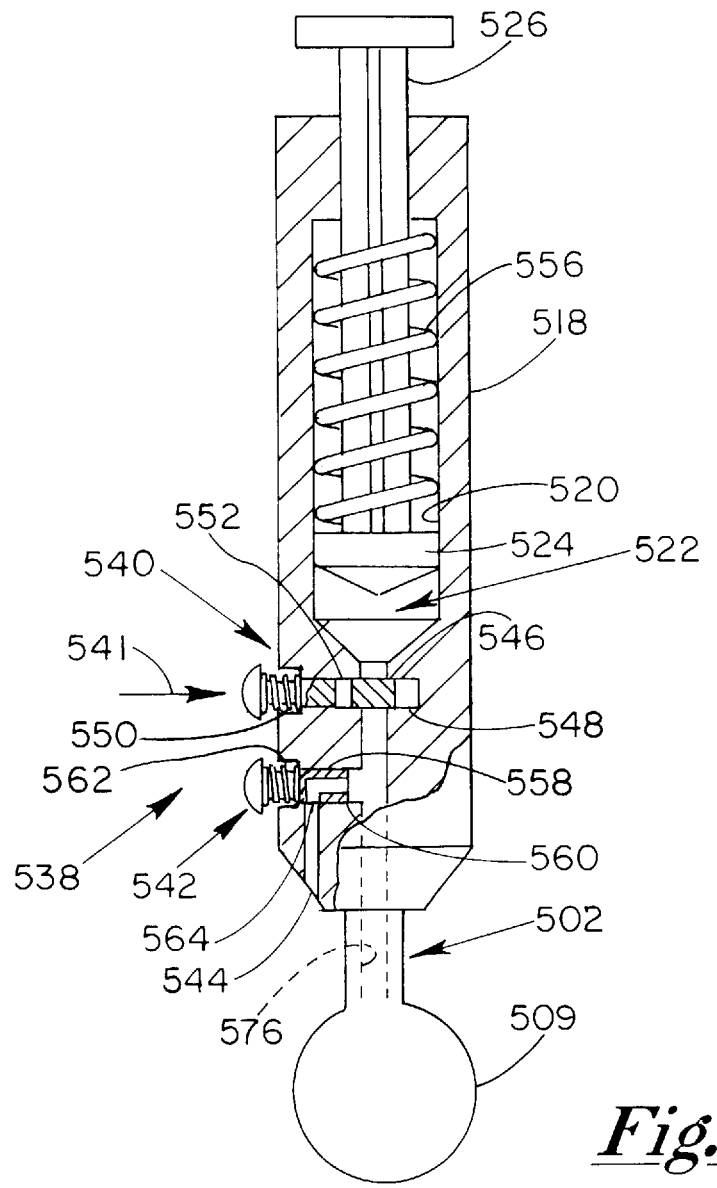
FIG. 30 is a sectional view of the tenth embodiment having a valve assembly to regulate fluid flow.

In FIG. 30, a valve assembly 538 regulates fluid flow through the passageway 516. In the embodiment illustrated, the valve assembly 538 includes a first valve 540 and a second valve 542. The first valve 540 selectively fluidly couples the chamber 522 with the expandable member or balloon 509, while the second valve 542 selectively fluidly couples the balloon 509 with a vent 544. The first valve 540 includes an elongated stem 546 slidably disposed in a recess 548. A spring 550 biases the elongated stem 546 such that a passageway 552 is positioned away from the passageway 516 and a portion of the elongated stem 546 blocks the passageway 516 When the first valve 540 is displaced in a direction indicated by arrow 541, the passageway 552 fluidly couples the chamber 522 with the passageway 516. Preferably, the piston 524 is biased with a spring 556 so that when the first valve 540 is operated, fluid is forced out of the chamber 522 to inflate the balloon 509.

The second valve 542 is used to deflate the balloon 509. The second valve 542 includes an elongated stem 558 slidably disposed in a passageway 560. A spring 562 biases the elongated stem 558 such that the passageway 516 and the vent 544 are sealed from each other. When the second valve 542 is displaced in a direction indicated by arrow 543, a passageway 564 formed in the elongated stem 558 fluidly couples the passageway 516 to the vent 544, allowing fluid from the balloon 509 to be expelled out through the vent 544.

Figure 31:
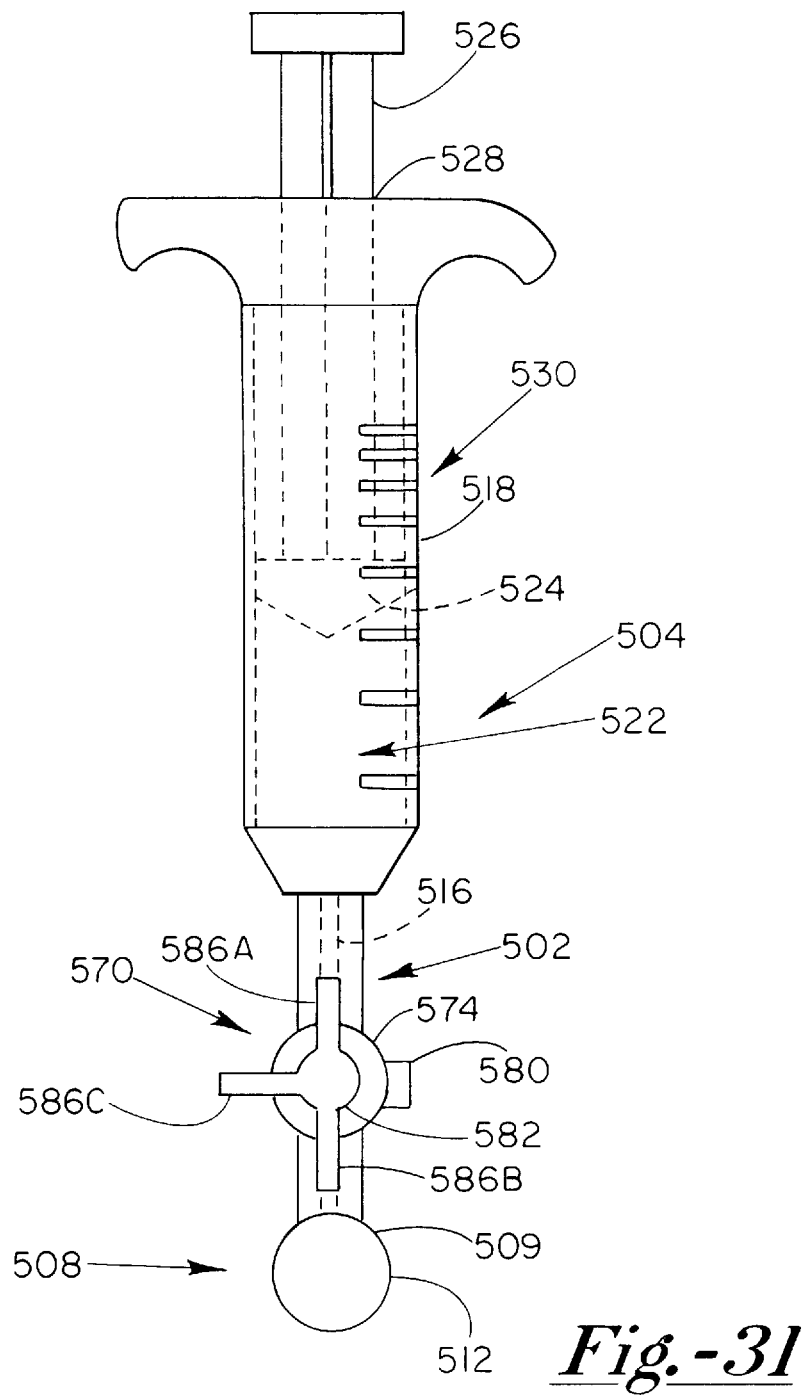
FIG. 31 is a side elevational view of the tenth embodiment with an alternative valve assembly to regulate fluid flow.
Figure 32:
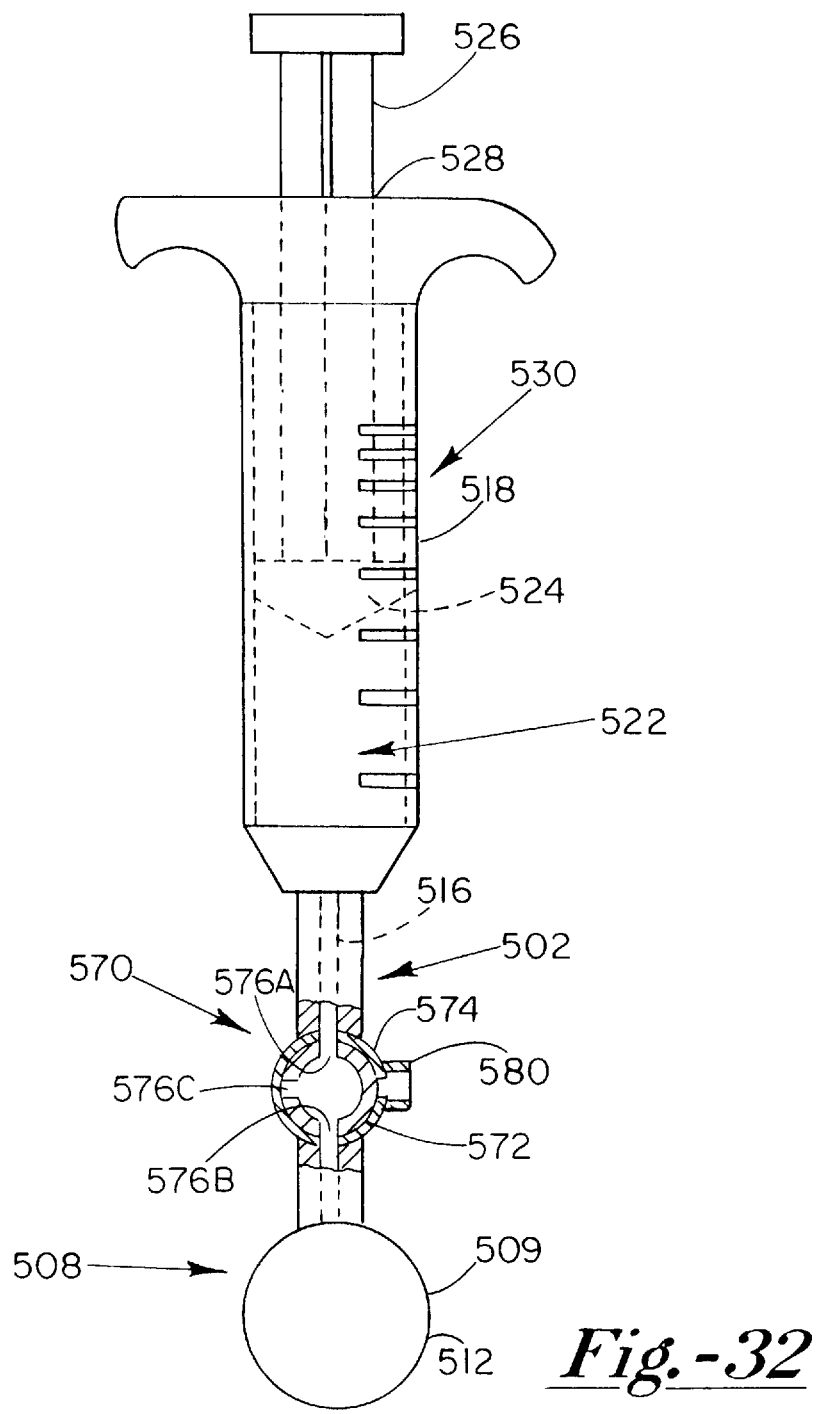
FIG. 32 is a side elevational view of the tenth embodiment with a portion broken away, illustrating the valve assembly in a first position.
Figure 33:
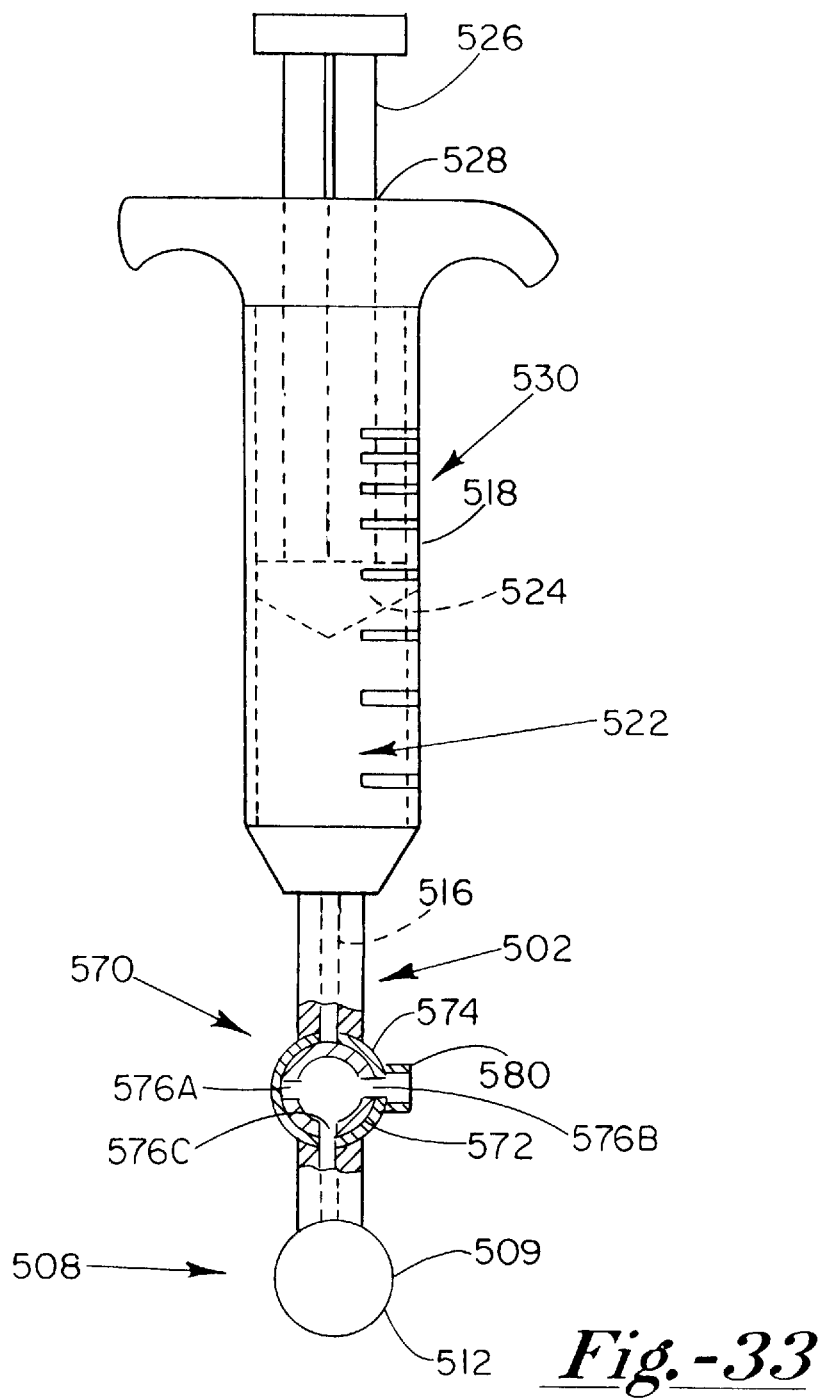
FIG. 33 is a side elevational view of the tenth embodiment with the portion broken away, illustrating the valve assembly in a second position.
Figure 34:
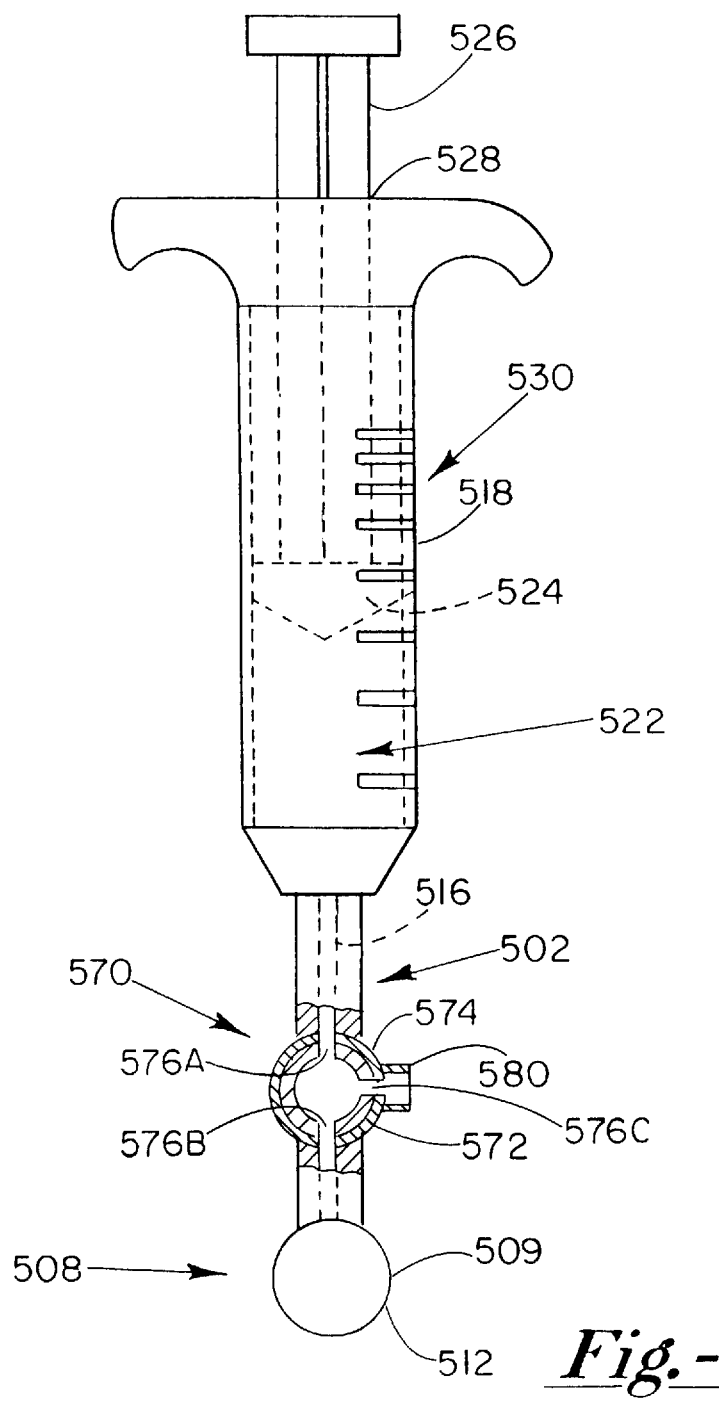
FIG. 34 is a side elevational view of the tenth embodiment with the portion broken away, illustrating the valve assembly in a third position.

An alternative valve assembly 570 to control fluid flow through the passageway 516 is illustrated in FIGS. 31–34. The valve assembly 570 includes an inner member 572 rotatable within an outer housing 574. The inner member 572 includes a T-shaped passageway having openings 576A, 576B and 576C. In FIG. 32, the inner member 572 is positioned to allow fluid flow through the openings 576A and 576B thereby fluidly coupling the balloon 509 to the chamber 522 to inflate the balloon. In FIG. 33, the inner member 572 is positioned so as to fluidly couple a vent 580 to the balloon 509 through the openings 576B and 576C, thereby deflating the balloon 509. In FIG. 34, the inner member 572 is positioned so as to fluidly couple the balloon 509, the chamber 522 and the vent 580 in order to deflate the balloon 509 and expel fluid from the chamber 522. A handle 582, illustrated in FIG. 31, is used to rotate the inner member 572 and has extensions 586A, 586B and 586C corresponding to the openings 576A, 576B and 576C, respectively.

Figure 35:
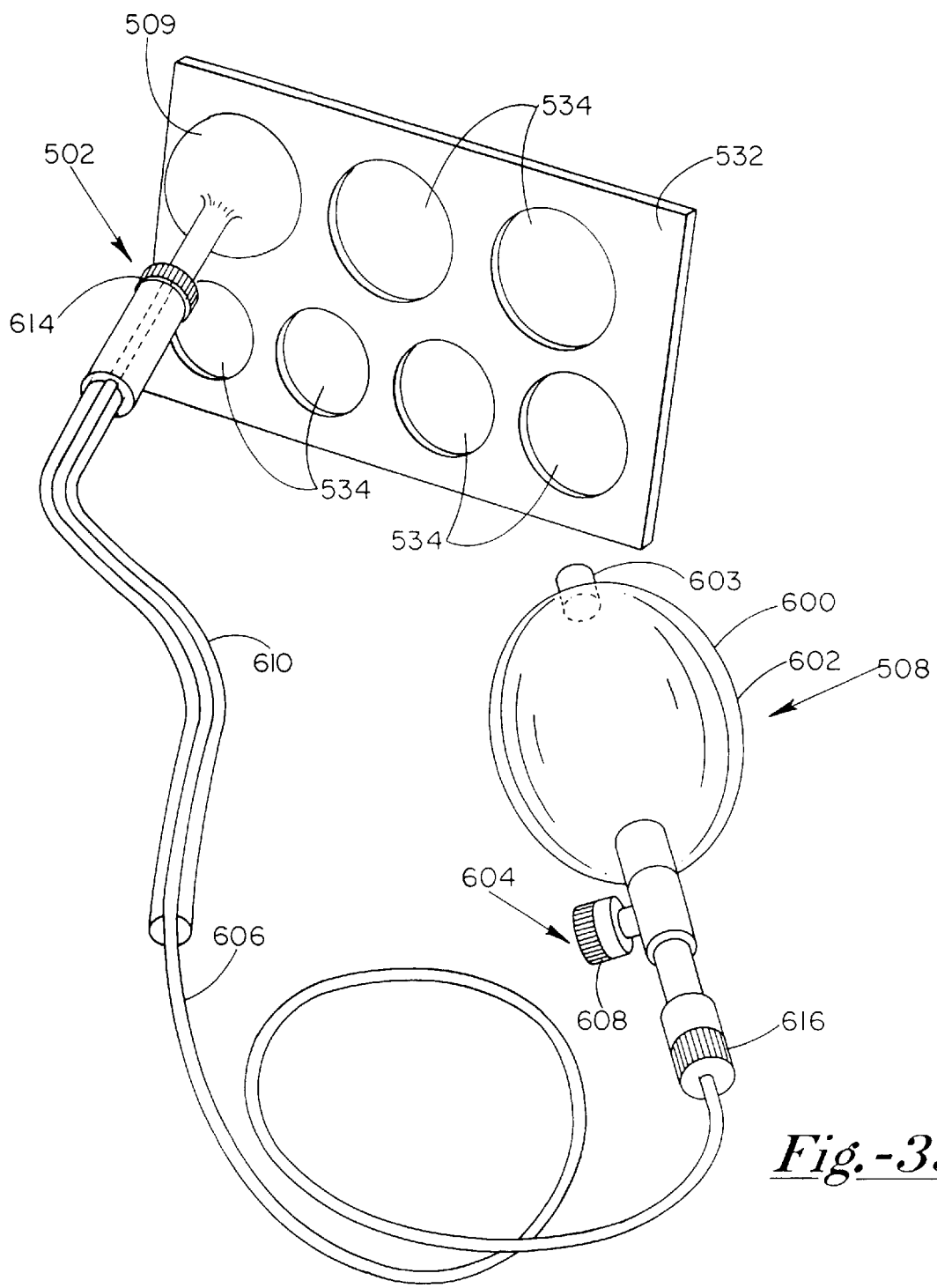
FIG. 35 is a perspective view of the tenth embodiment with an alternative pump.

In FIG. 35, the operator actuated movable member 504 comprises a hand operated pump 600. The pump 600 includes a compressible bulb 602. A valve assembly 604 fluidly couples fluid from the pump 600 to the elongated support member 502, preferably, through a flexible tube 606. The valve assembly 604 allows the bulb 602 to be compressed in order to expel a discrete quantity of fluid, such as air, from the bulb 602 into the balloon 509. When the bulb 602 is released, a check valve 603 allows the bulb 602 to expand again with air. The check valve 603 is closed during compression of the bulb 602 so fluid is forced to the balloon 509. Repeated compression and release of the bulb 602 provides successive, discrete quantities of air to the balloon 509. By inflating the balloon 509 with successive, discrete quantities of fluid, the balloon 509 can be inflated to any desired size. The pump 600 and valve assembly 604 are known and used for inflating blood pressure cuffs. The valve assembly 604 includes a relief valve 608 to deflate the balloon 509 when desired.

In a preferred embodiment, the elongated support member 502 includes a flexible shaft portion 610 formed from a material such as a shape memory metal, for example, a nickel titanium alloy. This material is flexible and allows the shaft portion 610 to be bent at an angle suitable for insertion into a chest cavity and to position the balloon 509 at a site of an excised native heart valve. The shaft portion 610 can be bent as many times as desired during surgery. Although the flexible tube 606 can be free from the shaft portion 610, preferably, the flexible tube 606 is supported by the shaft portion 610 in order that the tube 606 bends with the shaft portion 610. In the embodiment illustrated, a coupler 614 couples the balloon 509 to the support member 502, while a coupler 616 couples the support member 502 to the valve assembly 604. The couplers 614 and 616 allow the balloon 509, support member 502 and the valve assembly 604 to be separated for cleaning and re-sterilization. If desired, any of these components can be made disposable.

The apparatus of the present invention allows an attending physician to quickly ascertain the size of a tissue annulus. The apparatus of the present invention eliminates the requirement of using several sizers of fixed diameters to ascertain the size of the tissue annulus since only one sizer is required. This reduces the need for replacement of individual sizers, reduces the time for cleaning and sterilization, reduces the space required on the operating room tray and reduces the cost of manufacturing. Using the present apparatus, medical personnel simply adjust the sizing apparatus of the present invention until the desired size is determined. This reduces the time required to obtain the desired size, speeding up the sizing procedure significantly, thereby reducing exposure time for the patient. The present invention is particularly useful in sizing an excised native heart valve, because the tissue annulus is easy to access during surgery due to the position of the heart in the chest cavity.

Any of the embodiments can be used in minimally invasive procedures because the adjustable member of each embodiment can be reduced to its smallest diameter and passed through a trocar. Upon placement proximate the tissue annulus, the adjustable member can be expanded to size the tissue annulus and reduced again for removal. In addition, components of each embodiment can be made from materials suitable for cleaning and resterilization and/or materials suitable for disposal.

Although the present invention has been described with reference to preferred embodiments, workers skilled in the art will recognize that changes may be made in form and detail without departing from the spirit and scope of the invention. For example, other suitable ratchet mechanisms can be used in place of the ratchet mechanisms depicted.

What is claimed is:

1. A system for sizing tissue annulus, the system comprising:
   an elongated support member having a proximal end, a distal end and a passageway extending from the proximal end to the distal end;
   an operator actuated movable member joined to the proximal end of the elongated support member for providing fluid through the passageway to the distal end;
   an expandable member mounted to the distal end of the elongated support member and receiving the fluid, the expandable member having a reference axis and a substantially continuous outer curved surface disposed about the reference axis and selectively positionable in response to fluid provided by the operator actuated movable member between an inner position proximate the reference axis and an outer position spaced apart from the reference axis; and
   means for determining a dimension of the outer curved surface.

2. The system of claim 1 wherein the means for determining comprises a plate with a plurality of openings of varying size for receiving the expandable member.

3. The system of claim 1 further comprising a valve operably connected to the passageway for controlling fluid flow through the passageway.

4. The system of claim 3 wherein the valve controls fluid flow to the expandable member.

5. The system of claim 3 wherein the valve controls fluid flow from the expandable member to a vent.

6. The system of claim 1 wherein the operator actuated movable member comprises a housing having a chamber fluidly coupled to the passageway and a piston slidably disposed in the chamber.

7. The system of claim 6 wherein the means for determining includes determining a position of the piston in the chamber.

8. The system of claim 1 wherein the operator actuated movable member comprises a compressible bulb.

9. The system of claim 8 wherein the elongated support member comprises a flexible tube fluidly coupling the compressible bulb to the expandable member.

10. The system of claim 9 wherein the elongated support member includes a flexible support shaft.

11. A system for sizing tissue annulus, the system comprising:

an elongated support member having a proximal end and a distal end;

an operator actuated movable member joined to the proximal end of the elongated support member;

an adjustable member mounted to the distal end of the elongated support member, the adjustable member having a reference axis and a substantially continuous outer curved surface disposed about the reference axis and selectively positionable in response to the operator actuated movable member between an inner position proximate the reference axis and an outer position spaced apart from the reference axis; and a plate with a plurality of openings of varying size for receiving the adjustable member.

12. The system of claim 11 wherein the adjustable member comprises an expandable member, and wherein the elongated support member includes a passageway, and wherein the operator actuated movable member comprises means for providing fluid through the passageway to the expandable member.

* * * * *

UNITED STATES PATENT AND TRADEMARK OFFICE
CERTIFICATE OF CORRECTION

PATENT NO.   :   5,814,098
DATED        :   September 29, 1998
INVENTOR(S)  :   Hinnenkamp et al.

It is certified that error appears in the above-identified patent and that said Letters Patent is hereby corrected as shown below:

<u>TITLE PAGE</u>

[75] Inventors:

Delete "Thomas F. Hinnenkamp, White Bear Lake".

Signed and Sealed this

Nineteenth Day of January, 1999

Attest:

Attesting Officer

*Acting Commissioner of Patents and Trademarks*